(12) United States Patent
Garcia-Lopez et al.

(10) Patent No.: US 8,097,641 B2
(45) Date of Patent: Jan. 17, 2012

(54) HETEROCYCLYL SUBSTITUTED TETRAHYDRONAPHTHALENE DERIVATIVES AS 5-HT7 RECEPTOR LIGANDS

(75) Inventors: Monica Garcia-Lopez, Barcelona (ES); Antonio Torrens-Jover, Barcelona (ES); Helmut H. Buschmann, Barcelona (ES)

(73) Assignee: Laboratorios del Dr. Esteve, S.A., Barcelona (ES)

( * ) Notice: Subject to any disclaimer, the term of this patent is extended or adjusted under 35 U.S.C. 154(b) by 0 days.

(21) Appl. No.: 12/525,461

(22) PCT Filed: Feb. 6, 2008

(86) PCT No.: PCT/EP2008/000908
§ 371 (c)(1),
(2), (4) Date: Aug. 19, 2009

(87) PCT Pub. No.: WO2008/095689
PCT Pub. Date: Aug. 14, 2008

(65) Prior Publication Data
US 2010/0035936 A1 Feb. 11, 2010

(30) Foreign Application Priority Data
Feb. 6, 2007 (EP) .................................. 07384016

(51) Int. Cl.
*A61K 31/415* (2006.01)
*C07D 231/12* (2006.01)
(52) U.S. Cl. .................................... 514/406; 548/377.1
(58) Field of Classification Search .................. 514/345, 514/406, 378, 657; 548/377.1, 247; 564/428; 546/290
See application file for complete search history.

(56) References Cited

U.S. PATENT DOCUMENTS
2004/0127502 A1 7/2004 Blackburn et al.

FOREIGN PATENT DOCUMENTS
EP 1057814 A1 12/2000
WO 96/34849 A 11/1996

OTHER PUBLICATIONS

"Autism," [retrieved on May 14, 2008]. Retrieved online via Internet, URL: http://www.nlm.nih.gov/medlineplus/autism.html.*
"Anxiety," [retrieved on May 14, 2008]. Retrieved online via Internet, URL: http://www.nlm.nih.gov/medlineplus/anxiety.html.*
Patani et al., Bioisosterism: A Rational Approach in Drug Design, 1996, Chem. Rev., 96, pp. 3147-3176.*
International Search Report for PCT/EP2008/000908 dated Jun. 20, 2008.
Vermuelen, Erik S. et al; "Characterization of the 5-HT7 Receptor Determination of the Pharmacore for 5-HT7 Receptor Agonism and CoMFA-Based Modeling of the Agonist Binding Site"; Journal of Medicinal Chemistry; 2003; pp. 5365-5374; vol. 46, No. 25.
Holmberg, Paer et al; "Novel 2-Aminotetralin and 2-AminoChroman Derivatives as Selective Serotonin 5-HT7 Receptor Agonists and Antagonists"; Journal of Medicinal Chemistry; 2004; pp. 3927-3930; vol. 47, No. 16.
Itoh, Katsumi et al: "Synthesis and .beta.-adrenergic blocking activity of 2-(N-substituted amino)-1,2,3,4-tetrahydronaphthalen-1-ol derivatives"; Chemical and Pharmaceutical Bulletin; 1984; vol. 32, No. 1; Database Caplus, Chemical Abstracts Service, Columbus, Ohio.
Homan, Evert J. et al; "C5-Substituted derivatives of 5-OMe-BPAT: synthesis and interactions with dopamine D2 and serotonin 5-HT1A receptors"; Bioorganic and Medicinal Chemistry; 1999; pp. 2541-2548; vol. 7, No. 11.
Ghoneim, Ola M. et al; "Novel ligands for the human histamine H1 receptor: Synthesis, pharmacology, and comparative molecular field analysis studies of 2-dimethylamino-5-(6)-phenyl-1,2,3,4-tetrahydronaphthalenes"; Bioorganic and Medicinal Chemistry; 2006; pp. 6640-6658; vol. 14, No. 19.

* cited by examiner

*Primary Examiner* — Kamal Saeed
*Assistant Examiner* — Kristin Bianchi
(74) *Attorney, Agent, or Firm* — Heslin Rothenberg Farley & Mesiti P.C.

(57) ABSTRACT

The present invention relates to heterocyclyl-substituted-tetrahydro-naphthalen compounds of general formula (I), methods for their preparation, and compositions comprising these compounds as well as their use for the treatment or prophylaxis of various disorders in humans or animals.

30 Claims, No Drawings

HETEROCYCLYL SUBSTITUTED TETRAHYDRONAPHTHALENE DERIVATIVES AS 5-HT7 RECEPTOR LIGANDS

CROSS REFERENCE TO RELATED APPLICATIONS

This application is a U.S. National Phase filing under 35 U.S.C. §371 of International Application PCT/EP2008/000908, filed Feb. 6, 2008, and published as WO 2008/095689 on Aug. 14, 2008. PCT/EP2008/000908 claimed benefit of priority from European Patent Application No. EP 07384016.7, filed Feb. 6, 2007. The entire contents of each of the prior applications are incorporated herein by reference.

The present invention relates to heterocyclyl-substituted-tetrahydro-naphthalen compounds of general formula (I), methods for their preparation, medicaments comprising these compounds as well as their use for the preparation of a medicament for the treatment of humans or animals The search for new therapeutic agents has been greatly aided in recent years by better understanding of the structure of proteins and other biomolecules associated with target diseases. One important class of proteins that has been the subject of extensive study is the family of 5-hydroxytryptamine (serotonin, 5-HT) receptors. The 5-HT$_7$ receptor discovered in 1993 belongs to this family and has attracted great interest as a valuable new drug target (Terrón, J. A. *Idrugs*, 1998, vol. 1, no. 3, pages 302-310: "*The 5HT$_7$ receptor: A target for novel therapeutic avenues?*").

5-HT$_7$ receptors have been cloned from rat, mouse, guinea pig and human cDNA and exhibit a high degree of interspecies homology (approx. 95%), but it is unique in that it has a low sequence homology with other 5-HT receptors (less than 40%). Its expression pattern, in particular structures of the central nervous system (CNS) (highest in hypothalamus (in particular suprachiasmatic nuclei) and thalamus) and other peripheral tissues (spleen, kidney, intestinal, heart and coronary arthery), implicates the 5-HT$_7$ receptor in a variety of functions and pathologies. This idea is reinforced by the fact that several therapeutic agents, such as tricyclic antidepressants, typical and atypical antipsychotics and some 5-HT$_2$ receptor antagonists, display moderate to high affinity for both recombinant and functional 5-HT$_7$ receptors.

Functionally, the 5-HT$_7$ receptor has been implicated in regulation of circadian rhythms in mammals (Lovenberg, T. W. et al. *Neuron*, 1993, 11:449-458 "*A novel adenylyl cyclase-activating serotonin receptor (5-HT$_7$) implicated in the regulation of circadian rhythms*"). It is known that disruption of circadian rhythms is related to a number of CNS disorders including depression, seasonal affective disorder, sleep disorders, shift worker syndrome and jet lag among others.

Distribution and early pharmacological data also suggest that the 5-HT$_7$ receptor is involved in the vasodilatation of blood vessels. This has been demonstrated in vivo (Terrón, J. A., *Br J Pharmacol*, 1997, 121:563-571 "*Role of 5-HT$_7$ receptors in the long lasting hypotensive response induced by 5-hydroxytryptamine in the rat*"). Thus selective 5-HT$_7$ receptor agonists have a potential as novel hypertensive agents.

The 5-HT$_7$ receptor has also been related with the pathophysiology of migraine through smooth muscle relaxation of cerebral vessels (Schoeffter, P. et al., 1996, *Br J Pharmacol*, 117:993-994; Terrón, J. A., 2002, *Eur. J. Pharmacol.*, 439:1-11 "*Is the 5-HT$_7$ receptor involved in the pathogenesis and prophylactic treatment of migraine?*"). In a similar manner, involvement of 5-HT$_7$ in intestinal and colon tissue smooth muscle relaxation makes this receptor a target for the treatment of irritable bowel syndrome (De Ponti, F. et al., 2001, *Drugs*, 61:317-332 "*Irritable bowel syndrome. New agents targeting serotonin receptor subtypes*"). Recently, it has also been related to urinary incontinence (*British J. of Pharmacology*, September 2003, 140(1) 53-60: "*Evidence for the involvement of central 5HT-7 receptors in the micurition reflex in anaeshetized female rats*").

In view of the potential therapeutic applications of agonists or antagonists of the 5HT$_7$ receptor, a great effort has been directed to find selective ligands. Despite intense research efforts in this area, very few compounds with selective 5-HT$_7$ antagonist activity have been reported (Wesolowska, A., *Polish J. Pharmacol.*, 2002, 54: 327-341, "*In the search for selective ligands of 5-HT$_5$, 5-HT$_6$ and 5-HT$_7$ serotonin receptors*"), yet even fewer 5-HT7-Agonists.

There is still a need to find compounds that have pharmacological activity towards the receptor 5-HT$_7$, being both effective and selective, and having good "drugability" properties, i.e. good pharmaceutical properties related to administration, distribution, metabolism and excretion.

Thus, it was an object of the present invention to provide novel compounds that are suitable in particular as active substances in medicaments.

Said object was achieved by providing as an active compound a heterocyclyl-substituted-tetrahydro-naphthalen derivative of general formula (I) or its benzyl-substituted analogue of general formula (I$_{prot}$)

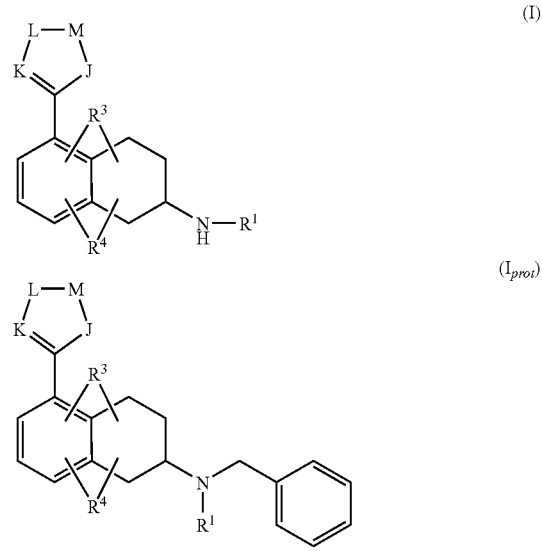

wherein
K-L-M-J together form
=CH—X—Y=CH—, in which any suitable H may be substituted by R$^6$ and/or R$^7$, and in which X is selected from NR$^8$, O or S, while Y is selected from N or CH;
=CH—X—Y—C(O)—, in which any suitable H may be substituted by R$^6$ and in which one of X and Y is NR$^8$, while the other is selected from NR$^{8a}$, S or O;
=CH—X—Y—C(O)—, in which one of X and Y is CH$_2$, while the other is selected from NR$^8$, S or O, in which any suitable H may be substituted by R$^6$ and/or R$^7$;
=CR$^6$—N=N—C(O)—; or =CR⁹—X₁=Y—X₂=CR⁹ᵃ—, in which two of Y, X₁ and X₂ are CH, while the other is selected from CH or N, in which any suitable H may be substituted by $R^6$;

$R^1$ is selected from the group consisting of hydrogen; a linear or branched, saturated or unsaturated, optionally at least mono-substituted aliphatic radical; or an optionally at least mono-substituted alkyl-aryl;

$R^3$ and $R^4$ are independently from each other selected from hydrogen; halogen, OH, SH, $NH_2$; a linear or branched, saturated or unsaturated, optionally at least mono-substituted aliphatic radical; or O—R with R being a linear or branched, saturated or unsaturated, optionally at least mono-substituted aliphatic radical;

$R^6$ and $R^7$ are independently from each other selected from hydrogen; halogen, OH, SH, $NH_2$; an aliphatic radical, which is linear or branched, saturated or unsaturated, and optionally at least mono-substituted by F, Cl, Br, I, SH or OH; or O—R with R being an aliphatic radical, which is linear or branched, saturated or unsaturated, and optionally at least mono-substituted by F, Cl, Br, I, SH or OH;

$R^8$ and $R^{8a}$ are independently from each other selected from hydrogen; or an aliphatic radical, which is linear or branched, saturated or unsaturated, and optionally at least mono-substituted by F, Cl, Br, I, SH or OH;

$R^9$ and $R^{9a}$ are independently from each other selected from hydrogen; halogen, OH, SH, $NH_2$; an aliphatic radical, which is linear or branched, saturated or unsaturated, and optionally at least mono-substituted by F, Cl, Br, I, SH or OH; or O—R with R being an aliphatic radical, which is linear or branched, saturated or unsaturated, and optionally at least mono-substituted by F, Cl, Br, I, SH or OH;

optionally in form of one of its stereoisomers, preferably enantiomers or diastereomers, its racemate or in form of a mixture of at least two of its stereoisomers, preferably enantiomers or diastereomers, in any mixing ratio, or a salt, preferably a physiologically acceptable salt thereof, or a corresponding solvate, respectively.

In another embodiment the compounds according to the invention according to formula (I) or ($I_{prot}$) are compounds, wherein K-L-M-J together form =CH—X—Y=CH—, in which any suitable H may be substituted by $R^6$ and/or $R^7$, and in which X is selected from $NR^8$, O or S, while Y is selected from N or CH;

=CH—X—Y—C(O)—, in which any suitable H may be substituted by $R^6$ and in which one of X and Y is $NR^8$, while the other is selected from $NR^{8a}$, S or O;

=CH—X—Y—C(O)—, in which one of X and Y is $CH_2$, while the other is selected from $NR^8$, S or O, in which any suitable H may be substituted by $R^6$ and/or $R^7$; or

=CR⁶—N=N—C(O)—;

$R^1$ is selected from the group consisting of hydrogen; a linear or branched, saturated or unsaturated, optionally at least mono-substituted aliphatic radical; or an optionally at least mono-substituted alkyl-aryl;

$R^3$ and $R^4$ are independently from each other selected from hydrogen; halogen, OH, SH, $NH_2$; a linear or branched, saturated or unsaturated, optionally at least mono-substituted aliphatic radical; or O—R with R being a linear or branched, saturated or unsaturated, optionally at least mono-substituted aliphatic radical;

$R^6$ and $R^7$ are independently from each other selected from hydrogen; halogen, OH, SH, $NH_2$; an aliphatic radical, which is linear or branched, saturated or unsaturated, and optionally at least mono-substituted by F, Cl, Br, I, SH or OH; or O—R with R being an aliphatic radical, which is linear or branched, saturated or unsaturated, and optionally at least mono-substituted by F, Cl, Br, I, SH or OH;

$R^8$ and $R^{8a}$ are independently from each other selected from hydrogen; or an aliphatic radical, which is linear or branched, saturated or unsaturated, and optionally at least mono-substituted by F, Cl, Br, I, SH or OH.

In another embodiment the compounds according to the invention according to formula (I) or ($I_{prot}$) are compounds, wherein K-L-M-J together form =CR⁹—X₁=Y—X₂=CR⁹ᵃ—, in which two of Y, X₁ and X₂ are CH, while the other is selected from CH or N, in which any suitable H may be substituted by $R^6$;

$R^1$ is selected from the group consisting of hydrogen; a linear or branched, saturated or unsaturated, optionally at least mono-substituted aliphatic radical; or an optionally at least mono-substituted alkyl-aryl;

$R^3$ and $R^4$ are independently from each other selected from hydrogen; halogen, OH, SH, $NH_2$; a linear or branched, saturated or unsaturated, optionally at least mono-substituted aliphatic radical; or O—R with R being a linear or branched, saturated or unsaturated, optionally at least mono-substituted aliphatic radical;

$R^6$ is selected from hydrogen; halogen, OH, SH, $NH_2$; an aliphatic radical, which is linear or branched, saturated or unsaturated, and optionally at least mono-substituted by F, Cl, Br, I, SH or OH; or O—R with R being an aliphatic radical, which is linear or branched, saturated or unsaturated, and optionally at least mono-substituted by F, Cl, Br, I, SH or OH;

$R^9$ and $R^{9a}$ are independently from each other selected from hydrogen; halogen, OH, SH, $NH_2$; an aliphatic radical, which is linear or branched, saturated or unsaturated, and optionally at least mono-substituted by F, Cl, Br, I, SH or OH; or O—R with R being an aliphatic radical, which is linear or branched, saturated or unsaturated, and optionally at least mono-substituted by F, Cl, Br, I, SH or OH; or $R^9$ is selected from halogen, OH, SH, $NH_2$; an aliphatic radical, which is linear or branched, saturated or unsaturated, and optionally at least mono-substituted by F, Cl, Br, I, SH or OH; or O—R with R being an aliphatic radical, which is linear or branched, saturated or unsaturated, and optionally at least mono-substituted by F, Cl, Br, I, SH or OH; and $R^{9a}$ is selected from hydrogen; halogen, OH, SH, $NH_2$; an aliphatic radical, which is linear or branched, saturated or unsaturated, and optionally at least mono-substituted by F, Cl, Br, I, SH or OH; or O—R with R being an aliphatic radical, which is linear or branched, saturated or unsaturated, and optionally at least mono-substituted by F, Cl, Br, I, SH or OH.

In one embodiment the following proviso applies to compounds according to the invention according to formula (I) or ($I_{prot}$):

If K-L-M-J together form =CR⁹—X₁=Y—X₂=CR⁹ᵃ—, in which two of Y, X₁ and X₂ are CH, while the other is selected from CH, $R^3$ and $R^4$ are hydrogen, and $R^9$ and $R^{9a}$ are $OCH_3$, then $R^1$ may not be hydrogen.

In another embodiment the following proviso applies to compounds according to the invention according to formula (I) or ($I_{prot}$):

If K-L-M-J together form =CR⁹—X₁=Y—X₂=CR⁹ᵃ—, in which two of Y, X₁ and X₂ are CH, while the other is selected from CH, one of $R^3$ or $R^4$ is hydrogen, while the other is $OCH_3$, and one of $R^9$ and $R^{9a}$ is hydrogen, while the other is Cl, then $R^1$ may not be methyl.

In another embodiment the following proviso applies to compounds according to the invention according to formula (I) or ($I_{prot}$):

If K-L-M-J together form $=CR^9-X_1=Y-X_2=CR^{9a}-$, in which $X_1$ and $X_2$ are CH, while Y is selected from $CR^6$ with $R^6$ being $CF_3$, one of $R^3$ or $R^4$ is hydrogen, while the other is $OCH_3$, and $R^9$ and $R^{9a}$ are hydrogen, then $R^1$ may not be methyl.

In another embodiment the following proviso applies to compounds according to the invention according to formula (I) or ($I_{prot}$):

If K-L-M-J together form $=CR^9-X_1=Y-X_2=CR^{9a}-$, in which two of Y, $X_1$ and $X_2$ are CH, while the other is selected from CH, one of $R^3$ or $R^4$ is hydrogen, while the other is OH, and $R^9$ and $R^{9a}$ are hydrogen, then $R^1$ may not be hydrogen or iso-propyl.

In a further embodiment the following one, some or all of the following provisos apply to compounds according to the invention according to formula (I) or ($I_{prot}$), in which K-L-M-J together form $=CR^9-X_1=Y-X_2=CR^{9a}-$, in which $X_1$ and $X_2$ are CH:

if Y is CH, $R^3$ and $R^4$ are hydrogen, and $R^9$ and $R^{9a}$ are $OCH_3$, then $R^1$ may not be hydrogen and/or if Y is CH, one of $R^3$ or $R^4$ is hydrogen, while the other is $OCH_3$, and one of $R^9$ and $R^{9a}$ is hydrogen, while the other is Cl, then $R^1$ may not be methyl; and/or if Y is $CR^6$ with $R^6$ being $CF_3$, one of $R^3$ or $R^4$ is hydrogen, while the other is $OCH_3$, and $R^9$ and $R^{9a}$ are hydrogen, then $R^1$ may not be methyl; and/or if Y is CH, one of $R^3$ or $R^4$ is hydrogen, while the other is OH, and R9 and $R^{9a}$ are hydrogen, then $R^1$ may not be hydrogen or iso-propyl.

The compound according to formula I may be present in the form of a racemic mixture as expressed by formula (I) or maybe present as one of the enantiomers. Thus Formula I may also be expressed as one of its enantiomers [(S) or (R)] thus as Formula I-S or Formula I-R.

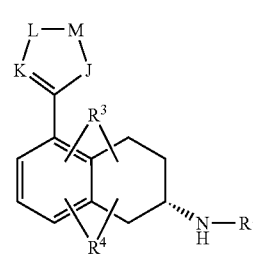

Formula I-S

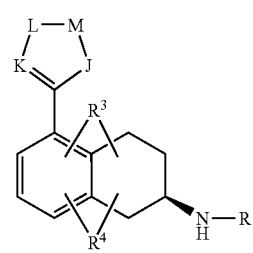

Formula I-R

The same applies to the compound according to formula $I_{prot}$, which thus may also be present as one of its enantiomers [(S) or (R)], thus as Formula $I_{prot}$—S or Formula $I_{prot}$—R.

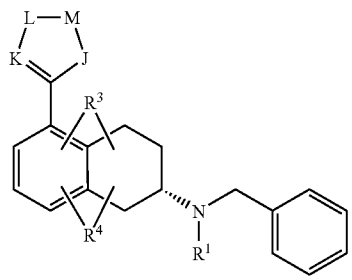

Formula $I_{prot}$-S

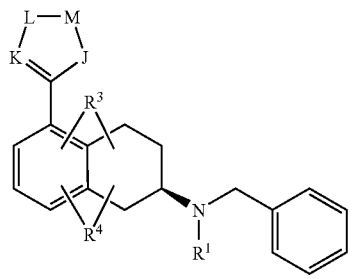

Formula $I_{prot}$-R

In a very preferred embodiment the compound or compounds according to the invention according to formula (I) or ($I_{prot}$) is/are 5-$HT_7$ receptor agonists.

A "mono- or polycyclic ring-system" according to the present invention means a mono- or polycyclic hydrocarbon ring-system that may be saturated, unsaturated or aromatic. If the ring system is polycyclic, each of its different rings may show a different degree of saturation, i.e. it may be saturated, unsaturated or aromatic. Optionally each of the rings of the mono- or polycyclic ring system may contain one or more heteroatoms as ring members, which may be identical or different and which can preferably be selected from the group consisting of N, O, S and P, more preferably be selected from the group consisting of N, O and S. Preferably the polycyclic ring-system may comprise two rings that are condensed. The rings of the mono- or polycyclic ring-sytem are preferably 5- or 6-membered.

An "aryl radical" or group is understood as meaning ring systems with at least one aromatic ring but without heteroatoms even in only one of the rings. Examples are phenyl, naphthyl, fluoranthenyl, fluorenyl, tetralinyl or indanyl, in particular 9H-fluorenyl or anthracenyl radicals, which can be unsubstituted or monosubstituted or polysubstituted.

"Alkyl-aryl" or "alkyl-aryl radical" or group is understood as meaning a ring system with at least one aromatic ring but without heteroatoms even in only one of the rings connected to the core through an alkylene $(CH_2)_{1-4}$ group. In this, substitution is referring to a substitution in the ring system, not in the alkylene. An example is benzyl, which can be unsubstituted or monosubstituted or polysubstituted.

In the context of this invention "cycloalkyl radical" or group is understood as meaning saturated and unsaturated (but not aromatic) cyclic hydrocarbons (without a heteroatom in the ring), which can be unsubstituted or mono- or polysubstituted. Furthermore, $C_{3-4}$-cycloalkyl represents $C_3$- or $C_4$-cycloalkyl, $C_{3-5}$-cycloalkyl represents $C_3$-, $C_4$- or $C_5$-cycloalky $C_{3-6}$-cycloalkyl represents $C_3$-, $C_4$-, $C_5$- or $C_6$-cycloalkyl, $C_{3-7}$-cycloalkyl represents $C_3$-, $C_4$-, $C_5$-, $C_6$- or $C_7$-cycloalkyl, $C_{3-8}$-cycloalkyl represents $C_3$-, $C_4$-, $C_5$-, $C_6$-, $C_7$- or $C_8$-cycloalkyl, $C_{4-5}$-cycloalkyl represents $C_4$- or $C_5$-cycloalkyl, $C_{4-6}$-cycloalkyl represents $C_4$-, $C_5$- or $C_6$-cycloalkyl, $C_{4-7}$-cycloalkyl represents $C_4$-, $C_5$-, $C_6$- or $C_7$-cycloalkyl, $C_{4-8}$-cycloalkyl represents $C_4$-, $C_5$-, $C_6$-$C_7$- or $C_8$-cycloalkyl $C_{5-6}$-cycloalkyl represents $C_5$- or $C_6$-cycloalkyl and $C_{5-7}$-cycloalkyl represents $C_5$-, $C_6$- or $C_7$-cycloalkyl. However, mono- or polyunsaturated, preferably monounsaturated, cycloalkyls also in particular fall under the term cycloalkyl as long as the cycloalkyl is not an aromatic system. The cycloalkyl radicals are preferably cyclopropyl, 2-methylcyclopropyl, cyclopropylmethyl, cyclobutyl, cyclopentyl, cyclopentylmethyl, cyclohexyl, cycloheptyl, cyclooctyl, and also adamantly.

A "heterocyclyl", a "heterocyclyl radical" or group or "heterocyclic ring system" is understood as meaning heterocyclic ring systems which contain one or more heteroatoms from the group consisting of nitrogen, oxygen and/or sulfur in the ring or ringsystem, and can also be mono- or polysubstituted. The ringsystem may consist either of only one saturated or unsaturated or even aromatic ring or may consist of 2, 3 or 4 saturated or unsaturated or even aromatic rings, which are condensed in that between two or more of the rings ring members are shared. Examples which may be mentioned from the group of heterocyclyls are furan, benzofuran, thiophene, benzothiophene, pyrrole, pyridine, pyrimidine, pyrazine, quinoline, isoquinoline, phthalazine, benzo-1,2,5-thiadiazole, imidazo-thiazole, benzothiazole, indole, benzotriazole, benzodioxolane, benzodioxane, carbazole and quinazoline.

In connection with mono- or polycyclic ring-system, alkylaryl, aryl radical, cycloalkyl radical, or heterocyclyl radical, "substituted" is understood—unless defined otherwise—as meaning replacement of at least one hydrogen radical on the ring-system of the mono- or polycyclic ring-system, the alkyl-aryl, the aryl radical, the cycloalkyl radical, or the heterocyclyl radical by OH, SH, $=$O, halogen (F, Cl, Br, I), CN, $NO_2$, COOH; $NR_xR_y$, with $R_x$ and $R_y$ independently being either H or a saturated or unsaturated, linear or branched, substituted or unsubstituted $C_{1-6}$-alkyl; by a saturated or unsaturated, linear or branched, substituted or unsubstituted $C_{1-6}$-alkyl; a saturated or unsaturated, linear or branched, substituted or unsubstituted —O—$C_{1-6}$-alkyl (alkoxy); a saturated or unsaturated, linear or branched, substituted or unsubstituted —S—$C_{1-6}$-alkyl; a saturated or unsaturated, linear or branched, substituted or unsubstituted —C(O)—$C_{1-6}$-alkyl; a saturated or unsaturated, linear or branched, substituted or unsubstituted —C(O)—O—$C_{1-6}$-alkyl; a substituted or unsubstituted phenyl. Within that "monosubstituted" means the substitution of exactly one hydrogen radical, whereas "polysubstituted" means the substitution of more than one hydrogen radical with "polysubstituted" radicals being understood as meaning that the replacement takes effect both on different and on the same atoms several times with the same or different substituents. Therefore, "optionally at least monsubstituted" means either "not substituted" if the option is not fulfilled, "monosubstituted" or "polysubstituted".

In connection with aryl radical, cycloalkyl radical, or heterocyclyl radical, "condensed with" is understood as meaning that the ring-system of the aryl radical, the cycloalkyl radical, or the heterocyclyl radical is sharing two atoms (one) of its ring(s) with a ring of the mono- or polycyclic ring-system it is condensed with.

Aliphatic radicals/groups, as referred to in the present invention, are optionally mono- or polysubstituted and may be branched or linear, saturated or unsaturated. Aliphatic radicals, as defined in the present invention, include alkyl, alkenyl and alkinyl radicals. Unsaturated aliphatic radicals, as defined in the present invention, include alkenyl and alkinyl radicals. Preferred aliphatic radicals according to the present invention include but are not restricted to methyl, ethyl, vinyl (ethenyl), ethinyl, propyl, n-propyl, isopropyl, allyl (2-propenyl), 1-propinyl, methylethyl, butyl, n-butyl, iso-butyl, sec-butyl, tert-butyl butenyl, butinyl, 1-methylpropyl, 2-methylpropyl, 1,1-dimethylethyl, pentyl, n-pentyl, 1,1-dimethylpropyl, 1,2-dimethylpropyl, 2,2-dimethylpropyl, hexyl, 1-methylpentyl, n-heptyl, n-octyl, n-nonyl and n-decyl.

In the context of this invention, alkyl radical or group is understood as meaning saturated, linear or branched hydrocarbons, which can be unsubstituted or mono- or polysubstituted. Thus unsaturated alkyl is understood to encompass alkenyl and alkinyl groups, like e.g.—CH$=$CH—$CH_3$ or —C$\equiv$C—$CH_3$, while saturated alkyl encompasses e.g. —$CH_3$ and —$CH_2$—$CH_3$. In these radicals, $C_{1-2}$-alkyl represents $C_1$- or $C_2$-alkyl, $C_{1-3}$-alkyl represents $C_1$-, $C_2$- or $C_3$-alkyl, $C_{1-4}$-alkyl represents $C_1$-, $C_2$-, $C_3$- or $C_4$-alkyl, $C_{1-5}$-alkyl represents $C_1$-, $C_2$-, $C_3$-, $C_4$-, or $C_5$-alkyl, $C_{1-6}$-alkyl represents $C_1$-, $C_2$-, $C_3$-, $C_4$-, $C_5$- or $C_6$-alkyl, $C_{1-7}$-alkyl represents $C_1$-, $C_2$-, $C_3$-, $C_4$-, $C_5$-, $C_6$- or $C_7$-alkyl, $C_{1-8}$-alkyl represents $C_1$-, $C_2$-, $C_3$-, $C_4$-, $C_5$-, $C_6$-, $C_7$- or $C_8$-alkyl, $C_{1-10}$-alkyl represents $C_1$-, $C_2$-, $C_3$-, $C_4$-, $C_5$-, $C_6$-, $C_7$-, $C_8$-, $C_9$- or $C_{10}$-alkyl and $C_{1-18}$-alkyl represents $C_1$-, $C_2$-, $C_3$-, $C_4$-, $C_5$-, $C_6$-, $C_7$-, $C_8$-, $C_9$-, $C_{10}$-, $C_{11}$-, $C_{12}$-, $C_{13}$-, $C_{14}$-, $C_{15}$, $C_{16}$-, $C_{17}$-or $C_{18}$-alkyl. The alkyl radicals are preferably methyl, ethyl, vinyl (ethenyl), propyl, allyl (2-propenyl), 1-propinyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, if substituted also $CHF_2$, $CF_3$ or $CH_2OH$ etc.

In connection with alkyl, alkylene or aliphatic radical or group—unless defined otherwise—the term "substituted" in the context of this invention is understood as meaning replacement of at least one hydrogen radical by F, Cl, Br, I, $NH_2$, SH or OH; within that "monosubstituted" means the substitution of exactly one hydrogen radical, whereas "polysubstituted" means the substitution of more than one hydrogen radical with "polysubstituted" radicals being understood as meaning that the replacement takes effect both on different and on the same atoms several times with the same or different substituents, for example three times on the same C atom, as in the case of $CF_3$, or at different places, as in the case of e.g. —CH(OH)—CH$=$CH—$CHCl_2$. Therefore, "optionally at least monsubstituted" means either "not substituted" if the option is not fulfilled, "monosubstituted" or "polysubstituted".

The term "alkylene" is understood as meaning a divalent alkyl group like —$CH_2$— or —$CH_2$—$CH_2$—, with $(CH_2)_{3-6}$ being understood as meaning —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and —$CH_2$—$CH_2$—$CH_2$—$CH_2$—$CH_2$—$CH_2$—, $(CH_2)_{1-4}$ is to be understood as meaning —$CH_2$—, —$CH_2$—$CH_2$—, —$CH_2$—$CH_2$—$CH_2$— and —$CH_2$—$CH_2$—$CH_2$—$CH_2$—, $(CH_2)_{4-5}$ is to be understood as meaning —$CH_2$—$CH_2$—$CH_2$—$CH_2$— and —$CH_2$—$CH_2$—$CH_2$—$CH_2$—$CH_2$—, etc.

The term "salt" is to be understood as meaning any form of the active compound used according to the invention in which it assumes an ionic form or is charged and is coupled with a counter-ion (a cation or anion) or is in solution. By this are also to be understood complexes of the active compound with other molecules and ions, in particular complexes which are complexed via ionic interactions.

The term "physiologically acceptable salt" means in the context of this invention any salt that is physiologically tolerated (most of the time meaning not being toxic—especially not caused by the counter-ion) if used appropriately for a treatment especially if used on or applied to humans and/or mammals.

These physiologically acceptable salts can be formed with cations or bases and in the context of this invention is understood as meaning salts of at least one of the compounds used according to the invention—usually a (deprotonated) acid—as an anion with at least one, preferably inorganic, cation which is physiologically tolerated—especially if used on humans and/or mammals. The salts of the alkali metals and alkaline earth metals are particularly preferred, and also those with NH4, but in particular (mono)- or (di)sodium, (mono)- or (di)potassium, magnesium or calcium salts.

These physiologically acceptable salts can also be formed with anions or acids in the context of this invention is understood as meaning salts of at least one of the compounds used according to the invention—usually protonated, for example on the nitrogen—as the cation with at least one anion which are physiologically tolerated—especially if used on humans and/or mammals. By this is understood in particular, in the context of this invention, the salt formed with a physiologically tolerated acid, that is to say salts of the particular active compound with inorganic or organic acids which are physiologically tolerated—especially if used on humans and/or mammals. Examples of physiologically tolerated salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid or citric acid.

The compounds of the invention may be in crystalline form or either as free compounds or as solvates and it is intended that those forms are within the scope of the present invention. Methods of solvation are generally known within the art. Suitable solvates are pharmaceutically acceptable solvates. The term "solvate" according to this invention is to be understood as meaning any form of the active compound according to the invention in which this compound has attached to it via non-covalent binding another molecule (most likely a polar solvent) especially including hydrates and alcoholates, e.g. methanolate.

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon or $^{15}N$-enriched nitrogen are within the scope of this invention.

Any compound that is a prodrug of a compound of formula (I) is within the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (April 2002).

The compounds of formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I) or, or of its salts, solvates or prodrugs.

Particularly preferred are compounds according to the invention of general formula (Ia) or of its benzyl-substituted analogue of general formula (Ia$_{prot}$)

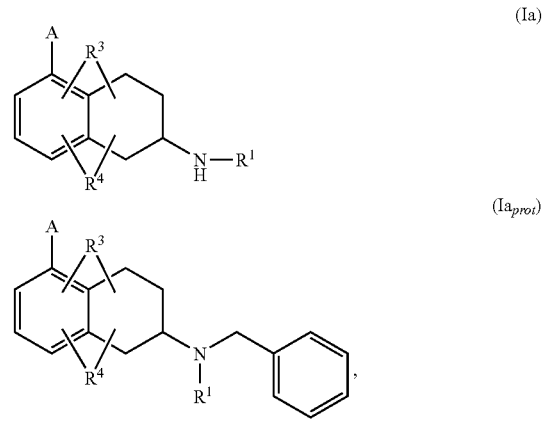

wherein
A is a compound selected from the following group

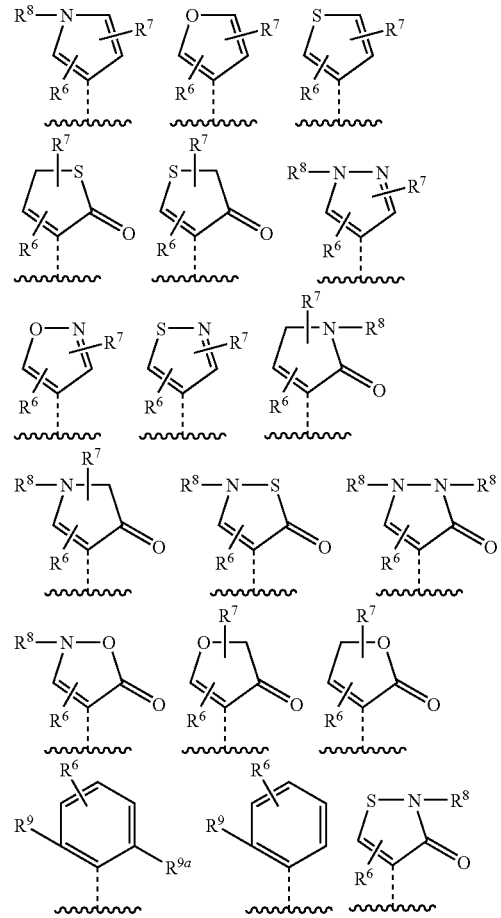

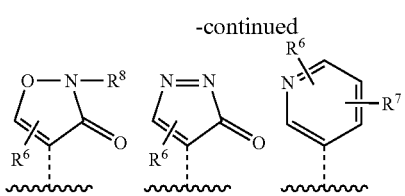

$R^1$ is selected from the group consisting of hydrogen; a linear or branched, saturated or unsaturated, optionally at least mono-substituted aliphatic radical; or an optionally at least mono-substituted alkyl-aryl;

$R^3$ and $R^4$ are independently from each other selected from hydrogen; halogen, OH, SH, $NH_2$; a linear or branched, saturated or unsaturated, optionally at least mono-substituted aliphatic radical; or O—R with R being a linear or branched, saturated or unsaturated, optionally at least mono-substituted aliphatic radical;

$R^6$ and $R^7$ are independently from each other selected from hydrogen; halogen, OH, SH, $NH_2$; an aliphatic radical, which is linear or branched, saturated or unsaturated, and optionally at least mono-substituted by F, Cl, Br, I, SH or OH; or O—R with R being an aliphatic radical, which is linear or branched, saturated or unsaturated, and optionally at least mono-substituted by F, Cl, Br, I, SH or OH;

$R^8$ and $R^{8a}$ are independently from each other selected from hydrogen; or an aliphatic radical, which is linear or branched, saturated or unsaturated, and optionally at least mono-substituted by F, Cl, Br, I, SH or OH;

$R^9$ and $R^{9a}$ are independently from each other selected from halogen, OH, SH, $NH_2$; an aliphatic radical, which is linear or branched, saturated or unsaturated, and optionally at least mono-substituted by F, Cl, Br, I, SH or OH; or O—R with R being an aliphatic radical, which is linear or branched, saturated or unsaturated, and optionally at least mono-substituted by F, Cl, Br, I, SH or OH.

In one embodiment the following proviso applies to compounds according to the invention according to formula (Ia) or ($Ia_{prot}$):
If A is

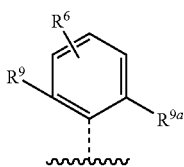

$R^6$ is hydrogen, $R^3$ and $R^4$ are hydrogen, and $R^9$ and $R^{9a}$ are $OCH_3$, then $R^1$ may not be hydrogen.

In one embodiment the following proviso applies to compounds according to the invention according to formula (Ia) or ($Ia_{prot}$):
If A is

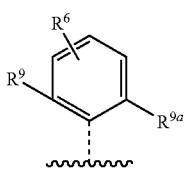

$R^6$ is hydrogen, one of $R^3$ or $R^4$ is hydrogen, while the other is $OCH_3$, and one of $R^9$ and $R^{9a}$ is hydrogen, while the other is Cl, then $R^1$ may not be methyl.

In another embodiment the following proviso applies to compounds according to the invention according to formula (Ia) or ($Ia_{prot}$):
If A is

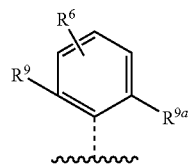

$R^6$ is hydrogen, one of $R^3$ or $R^4$ is hydrogen, while the other is OH, and $R^9$ and $R^{9a}$ are hydrogen, then $R^1$ may not be hydrogen or iso-propyl.

In a further embodiment one, some or all of the following provisos apply to compounds according to the invention according to formula (Ia) or ($Ia_{prot}$), wherein $R^6$ is hydrogen and A is

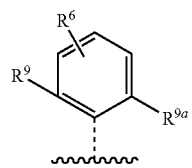

if $R^3$ and $R^4$ are hydrogen, and $R^9$ and $R^{9a}$ are $OCH_3$, then $R^1$ may not be hydrogen and/or if one of $R^3$ or $R^4$ is hydrogen, while the other is $OCH_3$, and one of $R^9$ and $R^{9a}$ is hydrogen, while the other is Cl, then $R^1$ may not be methyl; and/or if one of $R^3$ or $R^4$ is hydrogen, while the other is OH, and $R^9$ and $R^{9a}$ are hydrogen, then $R^1$ may not be hydrogen or iso-propyl.

Preferably A in the compound according to the invention according to formula (Ia) or ($Ia_{prot}$) is selected from

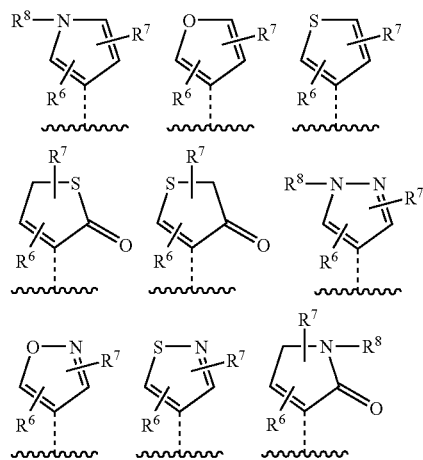

13

-continued

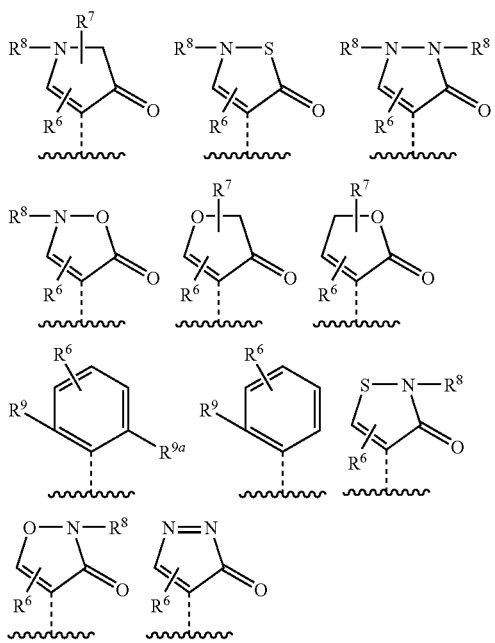

The compound according to formula Ia may be present in the form of a racemic mixture as expressed by formula (Ia) or maybe present as one of the enantiomers. Thus Formula Ia may also be expressed as one of its enantiomers [(S) or (R)] thus as Formula Ia-S or Formula Ia-R.

Formula Ia-S

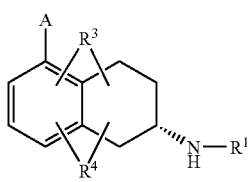

Formula Ia-R

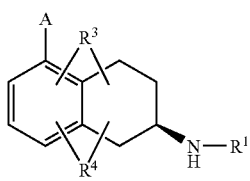

The same applies to the compound according to formula Ia$_{prot}$, which thus may also be present as one of its enantiomers [(S) or (R)], thus as Formula Ia$_{prot}$-S or Formula Ia$_{prot}$-R.

Formula Ia$_{prot}$-S

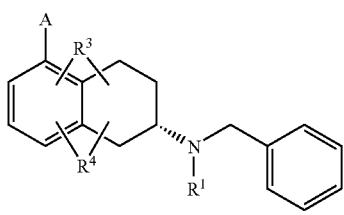

14

-continued

Formula Ia$_{prot}$-S

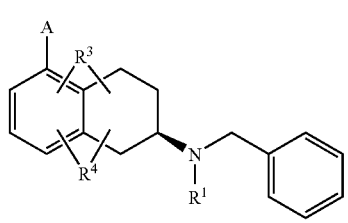

Also particularly preferred are compounds according to the invention of general formula (Ia) or (Ia$_{prot}$), wherein
A is a compound selected from the following group $R^1$ is selected from the group consisting of hydrogen; or a linear or branched, saturated or unsaturated, optionally at least mono-substituted aliphatic radical;

$R^3$ and $R^4$ are independently from each other selected from hydrogen; halogen, OH, SH, NH$_2$; a linear or branched, saturated or unsaturated, optionally at least mono-substituted aliphatic radical; or O—R with R being a linear or branched, saturated or unsaturated, optionally at least mono-substituted aliphatic radical;

$R^6$ and $R^7$ are independently from each other selected from hydrogen; halogen, OH, SH, NH$_2$; an aliphatic radical, which is linear or branched, saturated or unsaturated, and optionally at least mono-substituted by F, Cl, Br, I, SH or OH; or O—R with R being an aliphatic radical, which is linear or branched, saturated or unsaturated, and optionally at least mono-substituted by F, Cl, Br, I, SH or OH;

$R^8$ and $R^{8a}$ are independently from each other selected from hydrogen; or an aliphatic radical, which is linear or branched, saturated or unsaturated, and optionally at least mono-substituted by F, Cl, Br, I, SH or OH.

Also preferred are compounds according to the invention of general formula (Ia) or (Ia$_{prot}$), wherein A is a compound selected from the following group

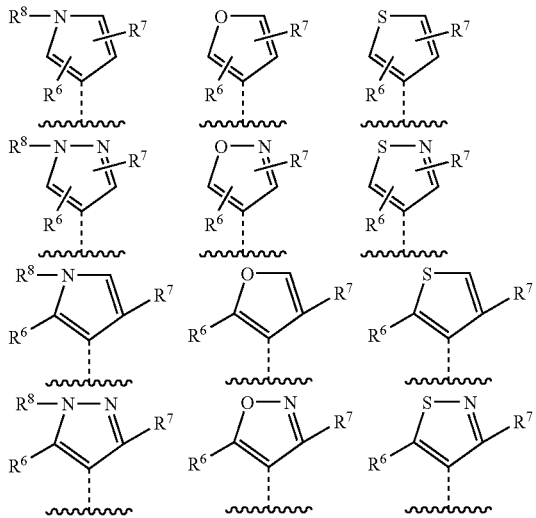

$R^1$ is selected from the group consisting of hydrogen; or a linear or branched, saturated or unsaturated, optionally at least mono-substituted aliphatic radical;

$R^3$ and $R^4$ are independently from each other selected from hydrogen; halogen, OH, SH, $NH_2$; a linear or branched, saturated or unsaturated, optionally at least mono-substituted aliphatic radical; or O—R with R being a linear or branched, saturated or unsaturated, optionally at least mono-substituted aliphatic radical;

$R^6$ and $R^7$ are independently from each other selected from hydrogen; halogen, OH, SH, $NH_2$; an aliphatic radical, which is linear or branched, saturated or unsaturated, and optionally at least mono-substituted by F, Cl, Br, I, SH or OH; or O—R with R being an aliphatic radical, which is linear or branched, saturated or unsaturated, and optionally at least mono-substituted by F, Cl, Br, I, SH or OH;

$R^8$ is selected from hydrogen; or an aliphatic radical, which is linear or branched, saturated or unsaturated, and optionally at least mono-substituted by F, Cl, Br, I, SH or OH.

Also preferred are compounds according to the invention of general formula (I), (I$_{prot}$), (Ia) or (Ia$_{prot}$), wherein $R^1$ is selected from the group consisting of hydrogen; or a linear or branched, optionally at least mono-substituted $C_{1-4}$-alkyl radical;

preferably $R^1$ is selected from the group consisting of hydrogen; or a linear or branched $C_{1-4}$-alkyl radical;

more preferably $R^1$ is selected from the group consisting of hydrogen, $CH_3$, $C_2H_5$ or $C_3H_7$;

most preferably $R^1$ is $CH_3$.

Also preferred are compounds according to the invention of general formula (I), (I$_{prot}$), (Ia) or (Ia$_{prot}$), wherein $R^3$ and $R^4$ are independently from each other selected from hydrogen; halogen, OH, SH, $NH_2$; a linear or branched, optionally at least mono-substituted $C_{1-4}$-alkyl radical; or O—R with R being a linear or branched, optionally at least mono-substituted $C_{1-4}$-alkyl radical;

preferably $R^3$ and $R^4$ are independently from each other selected from H, F, Cl, Br, I, OH, SH, $NH_2$, $CH_3$, $C_2H_5$, $C_3H_7$, $C_4H_9$, $OCH_3$, $OC_2H_5$, $OC_3H_7$ or $OC_4H_9$, more preferably $R^3$ and $R^4$ are H.

Also preferred are compounds according to the invention of general formula (I), (I$_{prot}$), (Ia) or (Ia$_{prot}$), wherein $R^6$ and $R^7$ are independently from each other selected from hydrogen; halogen, OH, SH, $NH_2$; a $C_{1-4}$-alkyl radical, which is linear or branched, and optionally at least mono-substituted by F, Cl, Br, I, SH or OH; or O—R with R being a $C_{1-4}$-alkyl radical, which is linear or branched, and optionally at least mono-substituted by F, Cl, Br, I, SH or OH;

preferably $R^6$ and $R^7$ are independently from each other selected from H, F, Cl, Br, I, OH, SH, $NH_2$, $CH_3$, $C_2H_5$, $C_3H_7$, $C_4H_9$, $OCH_3$, $OC_2H_5$, $OC_3H_7$ or $OC_4H_9$;

more preferably $R^6$ and $R^7$ are independently from each other selected from H, or $CH_3$.

Also preferred are compounds according to the invention of general formula (I), (I$_{prot}$), (Ia) or (Ia$_{prot}$), wherein $R^8$ is selected from hydrogen; or a $C_{1-4}$-alkyl radical, which is linear or branched, and optionally at least mono-substituted by F, Cl, Br, I, SH or OH;

preferably $R^8$ is selected from H, $CH_3$, $C_2H_5$, $C_3H_7$, or $C_4H_9$;

more preferably $R^8$ is selected from H or $CH_3$.

Also preferred are compounds according to the invention of general formula (Ia) or (Ia$_{prot}$), wherein A is selected from the following group

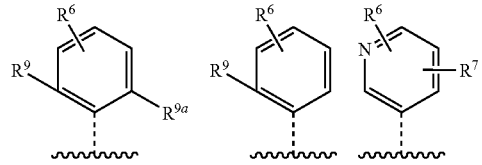

$R^1$ is selected from the group consisting of hydrogen; or a linear or branched $C_{1-4}$-alkyl radical; preferably in that $R^1$ is selected from the group consisting of hydrogen, $CH_3$, $C_2H_5$ or $C_3H_7$; most preferably in that $R^1$ is $CH_3$;

$R^3$ and $R^4$ are independently from each other selected from H, F, Cl, Br, I, OH, SH, $NH_2$, $CH_3$, $C_2H_5$, $C_3H_7$, $C_4H_9$, $OCH_3$, $OC_2H_5$, $OC_3H_7$ or $OC_4H_9$; most preferably in that $R^3$ and $R^4$ are H;

$R^6$ and $R^7$ are independently from each other selected from H, F, Cl, Br, I, OH, SH, $NH_2$, $CH_3$, $C_2H_5$, $C_3H_7$, $C_4H_9$, $OCH_3$, $OC_2H_5$, $OC_3H_7$ or $OC_4H_9$; most preferably in that $R^6$ and $R^7$ are independently from each other selected from H, or $OCH_3$.

$R^9$ and $R^{9a}$ are independently from each other selected from H, F, Cl, Br, I, OH, SH, $NH_2$, $CH_3$, $C_2H_5$, $C_3H_7$, $C_4H_9$, $OCH_3$, $OC_2H_5$, $OC_3H_7$ or $OC_4H_9$; most preferably in that $R^6$ and $R^7$ are independently from each other selected from H, Cl, F, or $OCH_3$.

Very preferred are compounds according to the invention of general formula (I), ($I_{prot}$), (Ia) or ($Ia_{prot}$), selected from
Methyl-[5-(1,3,5-trimethyl-1H-pyrazol-4-yl)-1,2,3,4-tetrahydro-naphthalen-2-yl]-amine,
(2S)-Methyl-[5-(1,3,5-trimethyl-1H-pyrazol-4-yl)-1,2,3,4-tetrahydro-naphthalen-2-yl]-amine,
Benzyl-[5-(1,3,5-trimethyl-1H-pyrazol-4-yl)-1,2,3,4-tetrahydro-naphthalen-2-yl]-amine,
(2S)-Benzyl-[5-(1,3,5-trimethyl-1H-pyrazol-4-yl)-1,2,3,4-tetrahydro-naphthalen-2-yl]-amine,
Benzyl-methyl-[5-(1,3,5-trimethyl-1H-pyrazol-4-yl)-1,2,3,4-tetrahydro-naphthalen-2-yl]-amine,
(2S)-Benzyl-methyl-[5-(1,3,5-trimethyl-1H-pyrazol-4-yl)-1,2,3,4-tetrahydro-naphthalen-2-yl]-amine;
5-(1,3,5-Trimethyl-1H-pyrazol-4-yl)-1,2,3,4-tetrahydro-naphthalen-2-ylamine hydrochloride; or
(2S)-5-(1,3,5-Trimethyl-1H-pyrazol-4-yl)-1,2,3,4-tetrahydro-naphthalen-2-ylamine hydrochloride;
most preferably selected from
(2S)-Methyl-[5-(1,3,5-trimethyl-1H-pyrazol-4-yl)-1,2,3,4-tetrahydro-naphthalen-2-yl]-amine,
(2S)-Benzyl-methyl-[5-(1,3,5-trimethyl-1H-pyrazol-4-yl)-1,2,3,4-tetrahydro-naphthalen-2-yl]-amine;
optionally in form of a salt, preferably a physiologically acceptable salt, more preferably in form of a physiologically acceptable acid addition salt, most preferably a hydrochloride salt, or a corresponding solvate.

Very preferred are compounds according to the invention of general formula (I), ($I_{prot}$), (Ia) or ($Ia_{prot}$), selected from
Methyl-[5-(1,3,5-trimethyl-1H-pyrazol-4-yl)-1,2,3,4-tetrahydro-naphthalen-2-yl]-amine,
(2S)-Methyl-[5-(1,3,5-trimethyl-1H-pyrazol-4-yl)-1,2,3,4-tetrahydro-naphthalen-2-yl]-amine,
Benzyl-[5-(1,3,5-trimethyl-1H-pyrazol-4-yl)-1,2,3,4-tetrahydro-naphthalen-2-yl]-amine,
(2S)-Benzyl-[5-(1,3,5-trimethyl-1H-pyrazol-4-yl)-1,2,3,4-tetrahydro-naphthalen-2-yl]-amine,
Benzyl-methyl-[5-(1,3,5-trimethyl-1H-pyrazol-4-yl)-1,2,3,4-tetrahydro-naphthalen-2-yl]-amine,
(2S)-Benzyl-methyl-[5-(1,3,5-trimethyl-1H-pyrazol-4-yl)-1,2,3,4-tetrahydro-naphthalen-2-yl]-amine;
5-(1,3,5-Trimethyl-1H-pyrazol-4-yl)-1,2,3,4-tetrahydro-naphthalen-2-ylamine;
(2S)-5-(1,3,5-Trimethyl-1H-pyrazol-4-yl)-1,2,3,4-tetrahydro-naphthalen-2-ylamine; or
Isopropyl-[5-(1,3,5-trimethyl-1H-pyrazol-4-yl)-1,2,3,4-tetrahydro-naphthalen-2-yl]-amine;
(2S)-Isopropyl-[5-(1,3,5-trimethyl-1H-pyrazol-4-yl)-1,2,3,4-tetrahydro-naphthalen-2-yl]-amine;
Methyl-[5-(1-methyl-1H-pyrazol-4-yl)-1,2,3,4-tetrahydro-naphthalen-2-yl]-amine;
[5-(3,5-Dimethyl-isoxazol-4-yl)-1,2,3,4-tetrahydro-naphthalen-2-yl]-methyl-amine;
[5-(2-Methoxy-phenyl)-1,2,3,4-tetrahydro-naphthalen-2-yl]-methyl-amine;
[5-(2-Chloro-6-methoxy-phenyl)-1,2,3,4-tetrahydro-naphthalen-2-yl]-methyl-amine;
[5-(2,6-Dichloro-phenyl)-1,2,3,4-tetrahydro-naphthalen-2-yl]-methyl-amine;
[5-(2,6-Difluoro-phenyl)-1,2,3,4-tetrahydro-naphthalen-2-yl]-methyl-amine; or
[5-(2-Methoxy-pyridin-3-yl)-1,2,3,4-tetrahydro-naphthalen-2-yl]-methyl-amine
most preferably
(2S)-Methyl-[5-(1,3,5-trimethyl-1H-pyrazol-4-yl)-1,2,3,4-tetrahydro-naphthalen-2-yl]-amine,
(2S)-Benzyl-methyl-[5-(1,3,5-trimethyl-1H-pyrazol-4-yl)-1,2,3,4-tetrahydro-naphthalen-2-yl]-amine;
optionally in form of a salt, preferably a physiologically acceptable salt, more preferably in form of a physiologically acceptable acid addition salt, most preferably a hydrochloride salt, or a corresponding solvate.

In another aspect, the present invention also provides a process for the preparation of compounds of general formula (I), wherein $R^1$, $R^3$, $R^4$, K, L, M and J have the meaning given above, according to which at least one compound of general formula II,

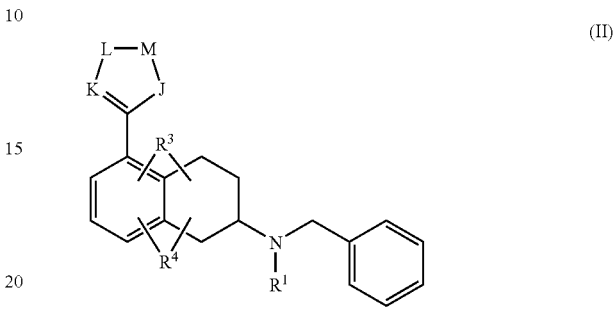

(II)

wherein $R^1$, $R^3$, $R^4$, K, L, M and J have the meaning given above, is subjected to benzyl cleavage by means of a hydrogenation reaction in the presence of a catalyst, especially a palladium catalyst, in a suitable reaction medium.

The compounds of general formula (II) can be prepared by catalytic cross-coupling reactions, which include the Kumada-Corriu-Tamao, Negishi, Stille, Hiyama, Suzuki-Miyaura, Heck, Sonogashira and other cross-coupling reactions known to those skilled in the art.

More preferably, preparation of compounds of general formula (II) can be achieved by reaction of at least one compound of general formula (III) or (IIIa)

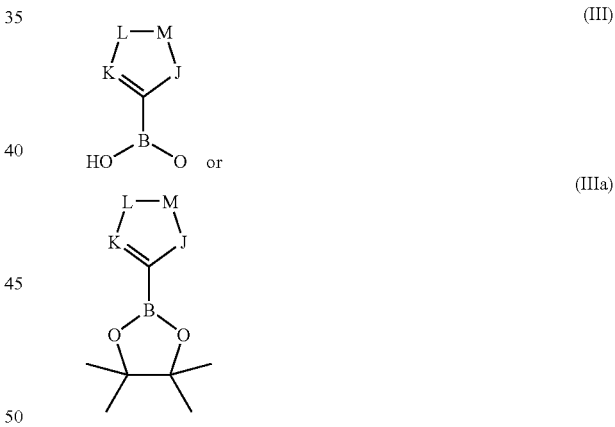

(III)

(IIIa)

wherein K, L, M and J have the meaning given above, by means of cross-coupling Suzuki reaction conditions with at least one compound of general formula (IV),

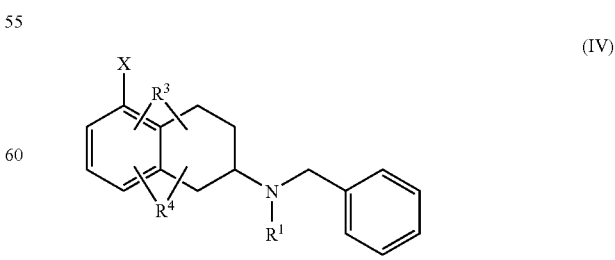

(IV)

wherein $R^1$, $R^3$, and $R^4$, have the meaning given above and X represent halogen, preferably bromide, OH, OMe or O-triflate group, in a suitable reaction medium, in the presence of a palladium catalyst, a suitable ligand and at least one base. This process can be performed by subjecting the reaction mixture to reflux by conventional heating for a period of time sufficient to achieve the title compound (II), or by microwave radiation, preferably for 1 to 10 minutes, and at a temperature between 100 to 120° C.

Preparation of compounds of general formula (IV) can be achieved by reductive amination reaction of aldehydes of general formula (V),

R¹CHO  (V)

wherein R¹ has the meaning given above, with a compound of general formula (VI),

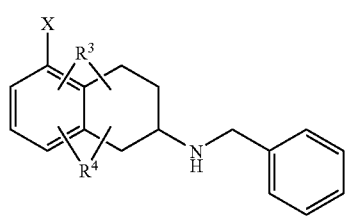

(VI)

wherein R³, R⁴, and X have the meaning given above. The reductive amination is performed by reaction of a mixture comprising a compound of general formula (V), and amino compound of general formula (VI) and a reducing agent in a suitable reaction medium, for a period of time sufficient to achieve the title compound (IV). The reductive amination reaction can also be performed under microwave radiation preferably for 1 to 10 minutes, and at a temperature between 90 to 120° C. The use of microwave irradiation limits the formation of undesirable secondary reaction products, compared to what is obtained in a conventional reductive amination procedure.

This process can be performed as a direct reaction when the carbonyl compound of general formula (V) and the amine compound of general formula (VI) are mixed with the reducing agent without prior formation of the intermediate imine or iminium salt. A stepwise or indirect reaction involves the reduction of the preformatted imine in a separate step.

The choice of the reducing agent can be conventionally made by those skilled in the art. Reducing agents useful in this procedure include hydrogen and a catalyst, zinc and HCl, sodium cyanoborohydride, lithium cyanoborohydride, tetrabutylammonium cyanoborohydride, cyanoborohydride on a solid support, sodium cyanoborohydride and dehydrating agents, sodium cyanoborohydride and titanium additives, sodium cyanoborohydride and zinc halide additives, sodium borohydride, sodium borohydride and dehydrating agents, sodium borohydride and titanium additives, sodium borohydride and zinc salt additives, lithium borohydride, potassium borohydride, polymer-supported borohydride, borohydride exchange resin with nickel acetate or palladium acetate, sodium triacetoxyborohydride, sodium triacetoxyborohydride and additives, tetramethylammonium triacetoxyborohydride, sodium cyano-9-borabicyclo[3.3.1]nonane, lithium triethylborohydride, lithium tri(sec-butyl)borohydride, sodium diisopinocampheylcyanoborohydride, amine boranes, borane-pyridine complex and alkylamine boranes. Sodium triacetoxyborohydride is particularly preferred because is non-toxic and generally does not reduce the carbonyl group prior to imine formation.

Compounds of general formula (VI) can be prepared by reductive amination reaction of benzylamine with a compound of general formula (VII),

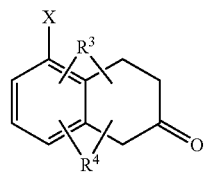

(VII)

wherein R³, R⁴, and X have the meaning given above. The reductive amination reaction could be performed following the methods described above.

The compounds of general formulas (III), (IIIa), (V) and (VII) are either commercially available or can be produced according to methods known to those skilled in the art.

Suitable reaction media are e.g. organic solvents, such as ethers, preferably diethyl ether, dioxane, tetrahydrofurane, dimethyl glycol ether, or alcohols, e.g. methanol, ethanol, propanol, isopropanol, butanol, isobutanol, tert-butanol, or hydrocarbons, preferably benzene, toluene, xylene, hexane, cyclohexane, petroleum ether, or halogenated hydrocarbons, e.g. dichloromethane, trichloromethane, tetrachloromethane, dichloroethylene, trichloroethylene, chlorobenzene or/and other solvents preferably ethyl acetate, triethylamine, pyridine, dimethulsulfoxide, dimethylformamide, hexamethylphosphoramide, acetonitrile, acetone or nitromethane are included. Mixtures based one or more of the above mentioned solvents and water may also be used.

According to the invention, the bases that may be used in the process are generally organic or inorganic bases, preferably alkali metal hydroxides, e.g. sodium hydroxide or potassium hydroxide, or obtained from other metals such as barium hydroxide or different carbonates, preferably potassium carbonate, sodium carbonate, calcium carbonate or alkoxydes, e.g. sodium methoxide potassium methoxide, sodium ethoxide, potassium ethoxide or potassium tert-butoxide, or organic amines, preferably triethylamine, diisopropylethylamine or heterocycles, e.g. 1,4-diazabicyclo[2.2.2]octane, 1,8-diazabicyclo5.4.0]undec-7-ene, pyridine, diamino pydine, dimethylaminopyridine, methylpiperidine or morpholine. Alkali metals such as sodium or its hydrides, e.g. sodium hydride, may also be used.

The preparation of compounds of general formula (I) is illustrated in scheme 1A:

Scheme 1A

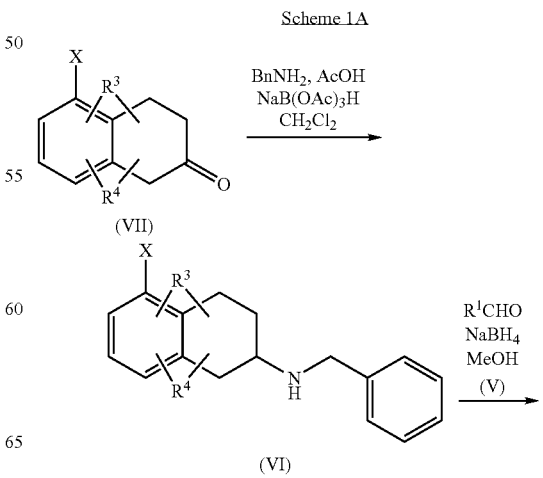

-continued

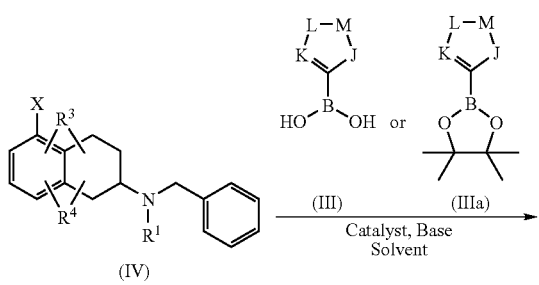

Scheme 1B

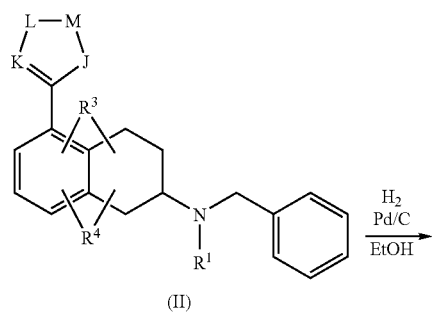

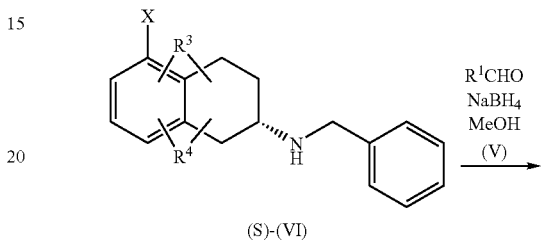

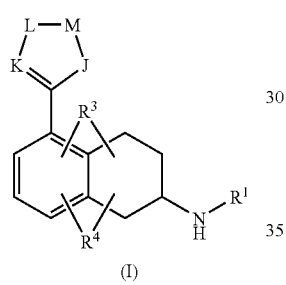

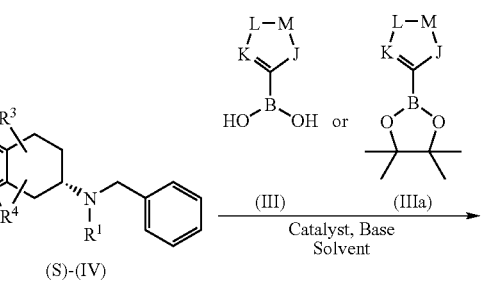

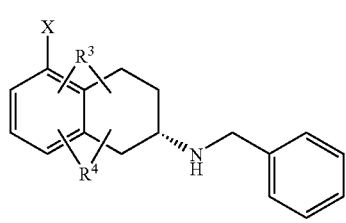

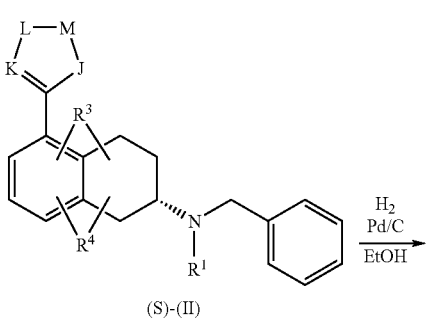

Enantiomerically pure compounds of general formula (S)-VI), (S)-(VI)

wherein X, $R^3$ and $R^4$ have the meaning described above, are obtained from racemic compounds of general formula (VI) by standard separation procedures known to those skilled in the art, e.g. chromatographic methods or crystallization with chiral reagents, preferably mandelic acid or di-p-toluyltartaric acid, as illustrated in Scheme 1B. Crystallization with (S)-(+)-mandelic acid leads to (S) enantiomer forms of compounds depicted in Scheme 1B, whereas crystallization with (R)-(−)-mandelic acid or L-di-p-toluyltartaric acid leads to (R) enantiomer forms of these compounds.

Subsequent preparation of enantiomerically pure compounds of general formula (S)-(I) may proceed as described above and is illustrated in Scheme 1B:

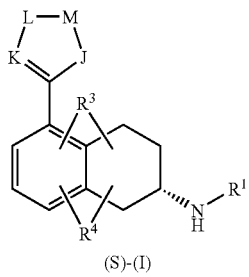

In another aspect, the present invention also provides a process for the preparation of compounds of general formula (I), in the particular case in which X is OH, OMe or O-triflate group, according to Scheme 2A.

Preparation of compounds of general formula (IVa),

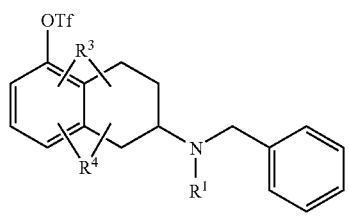
(IVa)

wherein $R^1$, $R^3$ and $R^4$ have the meaning described above, can be achieved by reaction of triflic anhydride, in the presence of a base and in a suitable reaction medium, with compounds of general formula (IVb),

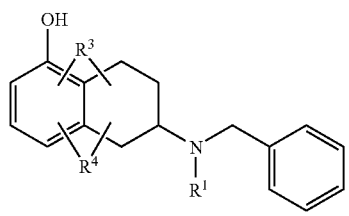
(IVb)

wherein $R^1$, $R^3$ and $R^4$ have the meaning described above.

Preparation of compounds of general formula (IVb) can be achieved by reductive amination reaction of aldehydes of general formula (V), $$R^1CHO \quad (V)$$

wherein $R^1$ have the meaning given above, with a compound of general formula (VIa),

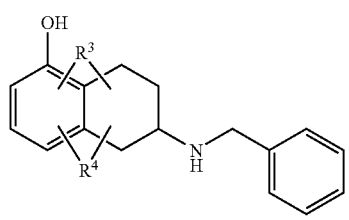
(VIa)

wherein $R^3$ and $R^4$ have the meaning described above. The reductive amination reaction could be performed following the methods described above.

Hydroxyl compounds of general formula (VIa) are obtained from the methoxy compounds of general formula (VIb) by heating in HBr 48% at 125° C.,

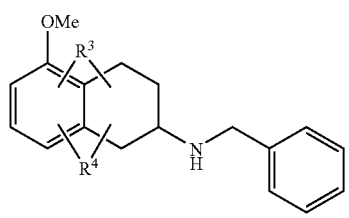
(VIb)

wherein $R^3$ and $R^4$ have the meaning described above. Demethylation of compounds of general formula (VIb) to obtain compounds of general formula (VIa) can also be achieved by reaction with $BBr_3$ in a suitable reaction medium, or by other methods known to those skilled in the art.

The bases that may be used in the process and the suitable reaction media are those described above.

This alternative method for the preparation of compounds of general formula (I) is illustrated in scheme 2A:

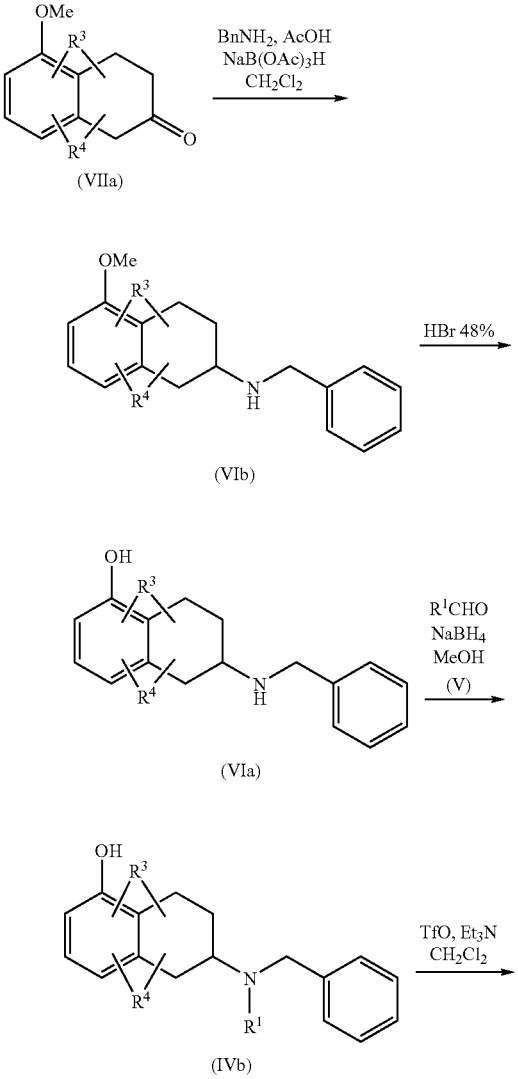

-continued

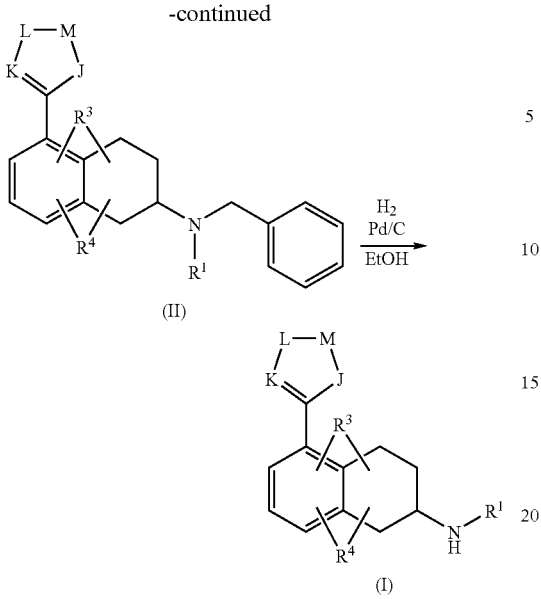

Enantiomerically pure compounds of general formula (S)-(VIb),

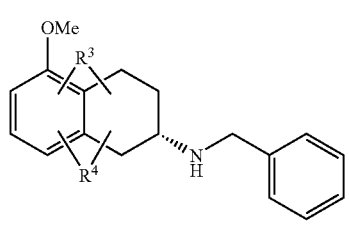

wherein R³ and R⁴ have the meaning described above, are obtained from racemic compounds of general formula (VIb) by standard separation procedures known to those skilled in the art, e.g. chromatographic methods or crystallization with chiral reagents, preferably mandelic acid or di-p-toluyltartaric acid, as illustrated in Scheme 2B. Crystallization with (S)-(+)-mandelic acid or L-di-p-toluyltartaric acid leads to (S) enantiomer forms of compounds depicted in Scheme 2B, whereas crystallization with (R)-(−)-mandelic acid leads to (R) enantiomer forms of these compounds.

Subsequent preparation of enantiomerically pure compounds of general formula (S)-(I) by this alternative method, may proceed as described above and is illustrated in Scheme 2B:

Scheme 2B

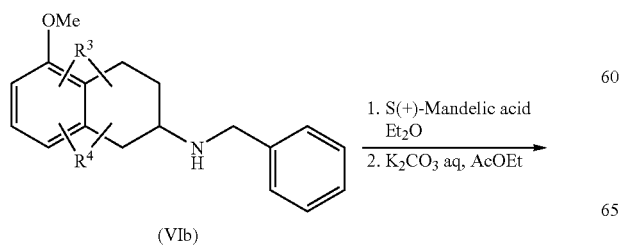

-continued

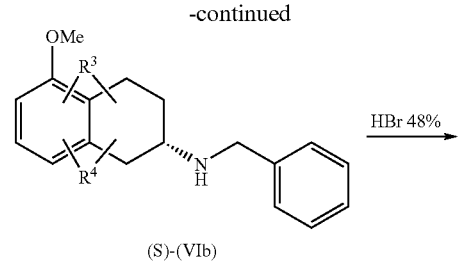

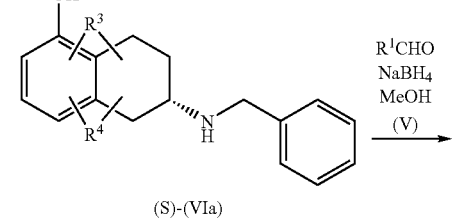

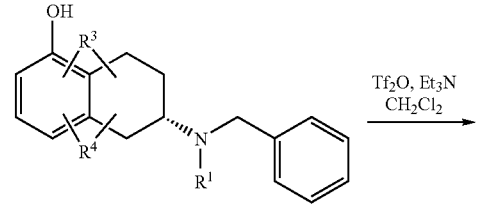

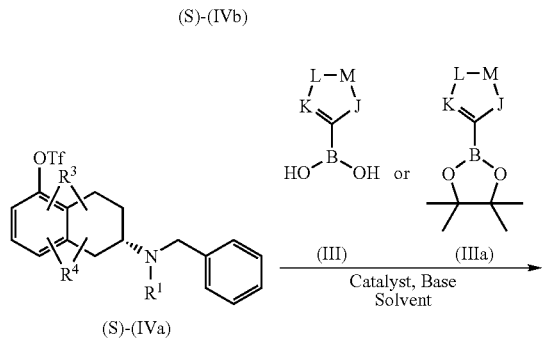

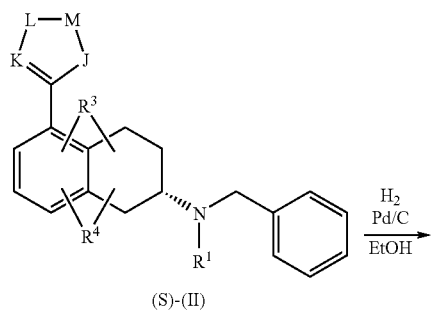

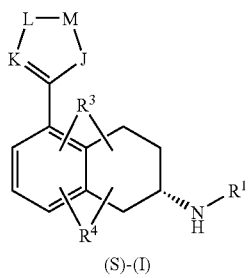

In another aspect, the present invention also provides a process for the preparation of compounds of general formula (I), in the particular case in which R¹ is —H, according to Scheme 3. As illustrated, amino compounds of general formula (I) can be obtained from compounds of general formula (VIII),

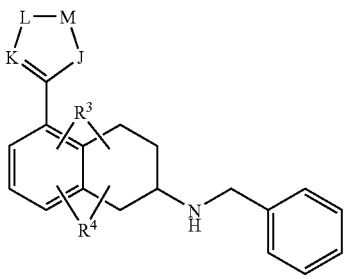

(VIII)

wherein R³, R⁴, K, L, M and J have the meaning described above, by means of a hydrogenation reaction in the presence of a catalyst, especially a palladium catalyst, in a suitable reaction medium.

Preparation of compounds of general formula (VIII) can be achieved by acidic cleavage of compounds of general formula (IX),

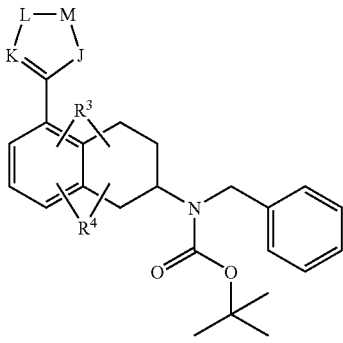

(IX)

wherein R³, R⁴, K, L, M and J have the meaning described above. These compounds can be prepared by reaction of at least one compound of general formula (III) or (IIIa)

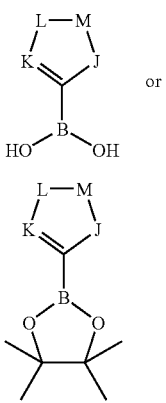

(III)

or (IIIa)

wherein K, L, M and J have the meaning given above, by means of cross-coupling Suzuki reaction conditions with at least one compound of general formula (X),

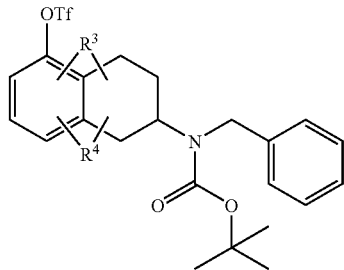

(X)

wherein R³ and R⁴, have the meaning given above, in a suitable reaction medium, in the presence of a palladium catalyst, a suitable ligand and at least one base. This process can be performed by subjecting the reaction mixture to reflux by conventional heating for a period of time sufficient to achieve the title compound (IX), or by microwave radiation, preferably for 1 to 10 minutes, and at a temperature between 100 to 120° C.

Preparation of compounds of general formula (X) can be achieved by reaction of triflic anhydride, in the presence of a base and in a suitable reaction medium, with compounds of general formula (XI),

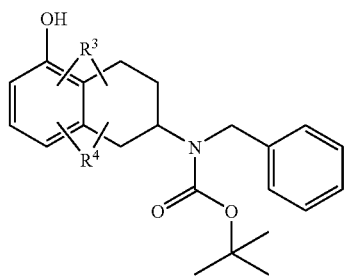

(XI)

wherein R³ and R⁴ have the meaning described above. Compounds of general formula (XI) are obtained from the above described compounds of general formula (VIa) by means of reaction with di-tert-butyl dicarbonate in the presence of a base and in a suitable reaction medium. Boc protecting group could also be introduced by other methods described in the literature [T. W. Greene and P. G. M. Wuts, Protective groups in organic synthesis, John Wiley & sons, 1999].

The compounds of general formulas (III) and (IIIa) are either commercially available or can be produced according to methods known to those skilled in the art.

The bases that may be used in the process and the suitable reaction media are those described above.

The preparation of compounds of general formula (I) in the particular case in which R¹ is H, is illustrated in scheme 3:

Scheme 3

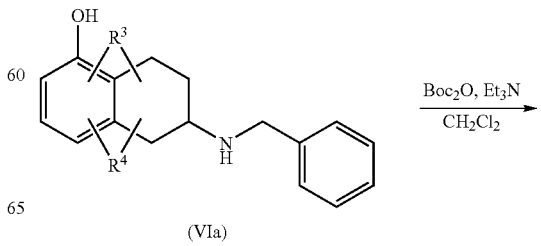

(VIa)

-continued

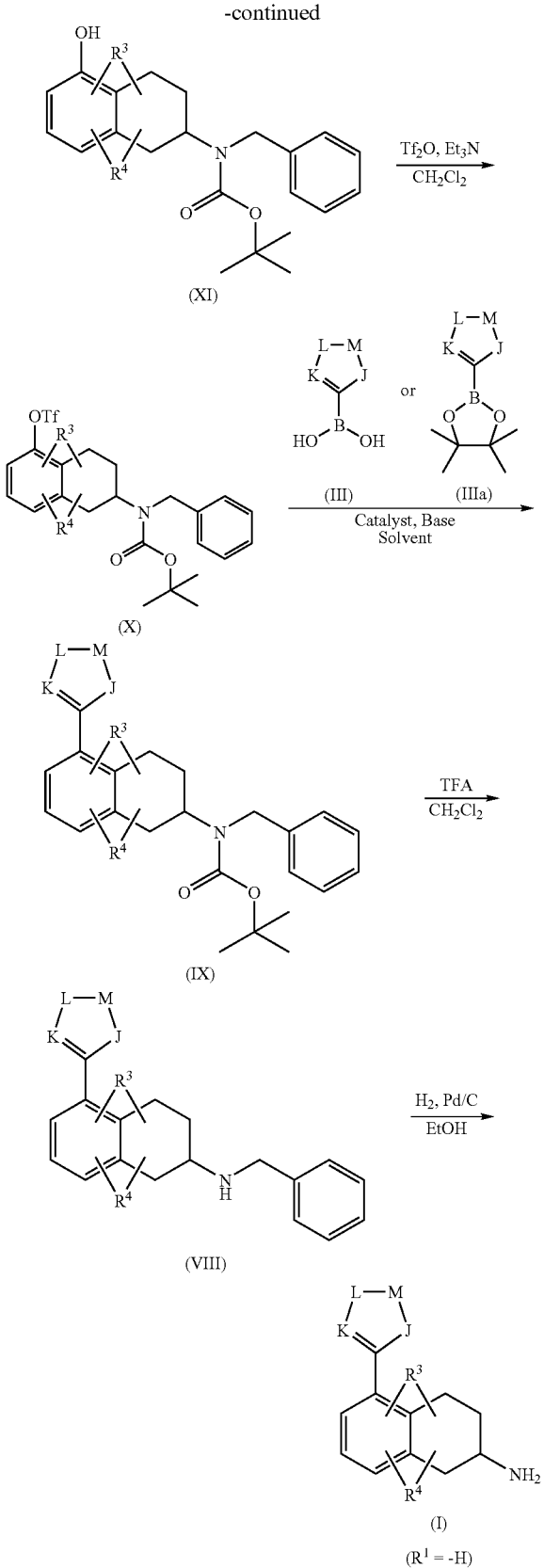

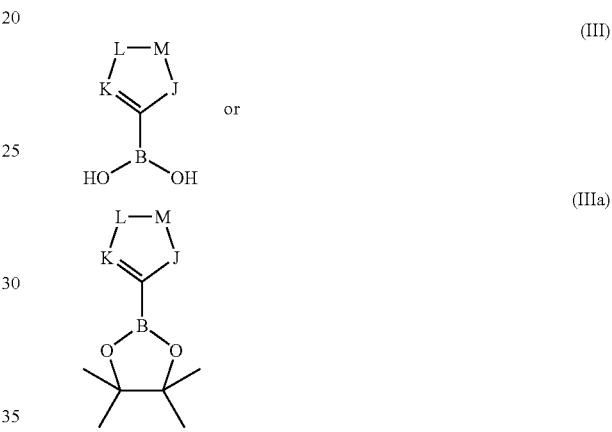

Scheme 3, by using compounds of general formula (S)-(VIa) or (R)-(VIa) as starting material. These compounds could be prepared from racemic compounds of general formula (VI) by standard separation procedures known to those skilled in the art, e.g. chromatographic methods or crystallization with chiral reagents, preferably mandelic acid or di-p-toluyltartaric acid, as described above.

In a further aspect, the present invention also provides an alternative process for the preparation of compounds of general formula (I), according to Scheme 4. The compounds of general formula (I) can be prepared by catalytic cross-coupling reactions, which include the Kumada-Corriu-Tamao, Negishi, Stille, Hiyama, Suzuki-Miyaura, Heck, Sonogashira and other cross-coupling reactions known to those skilled in the art.

More preferably the compounds of general formula (I) can be prepared by cross-coupling Suzuki reaction of boronic acids or boronate esters of general formula (III) or (IIIa),

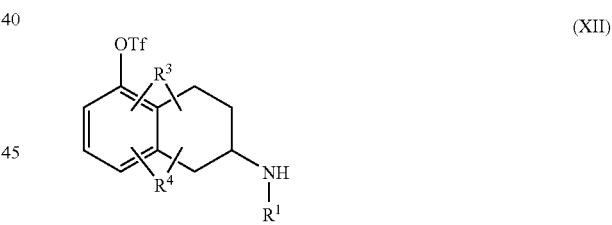

wherein K, L, M and J have the meaning given above, with at least one compound of general formula (XII),

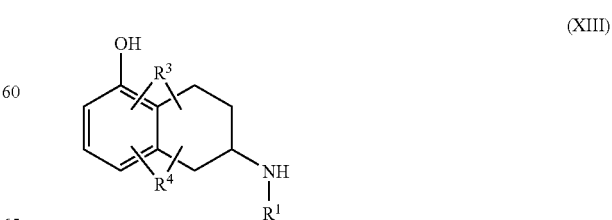

wherein $R^1$, $R^3$ and $R^4$ have the meaning given above, in a suitable reaction medium, in the presence of a palladium catalyst, a suitable ligand and at least one base.

Preparation of compounds of general formula (XII) can be achieved by reaction of triflic anhydride, in the presence of a base and in a suitable reaction medium, with compound of general formula (XIII), wherein $R^1$, $R^3$ and $R^4$ have the meaning given above.

Enantiomerically pure compounds of general formula (S)-(I) or (R)-(I) in the particular case in which $R^1$ is —H, could be obtained following the synthetic process illustrated in Preparation of compounds of general formula (XIII) can be achieved by reductive amination reaction of aldehydes of general formula (V),

R¹CHO (V)

wherein R¹ has the meaning given above, with a compound of general formula (XIV),

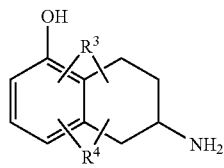

(XIV)

wherein R³ and R⁴ have the meaning given above.

Compounds of general formula (XIV) can be obtained by subjecting compounds of general formula (VIa),

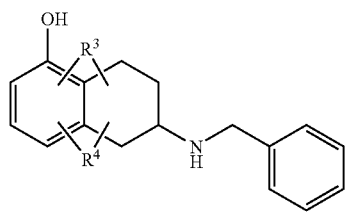

(VIa)

wherein R³ and R⁴ have the meaning given above, to benzyl cleavage by means of a hydrogenation reaction in the presence of a catalyst, especially a palladium catalyst, in a suitable reaction medium.

Starting compounds of general formula (VIa) can be prepared as described above (scheme 2A).

The compounds of general formula (III), (IIIa) and (V) are either commercially available or can be produced according to methods known to those skilled in the art.

Suitable reaction media are those described above.

The bases and reducing agents that may be used in the process are those described above.

This alternative method for the preparation of compounds of general formula (I) is illustrated in scheme 4:

Scheme 4

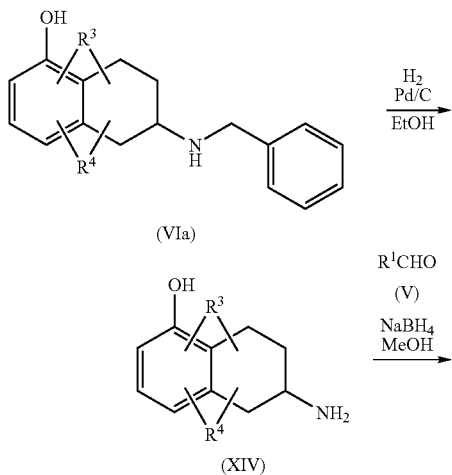

-continued

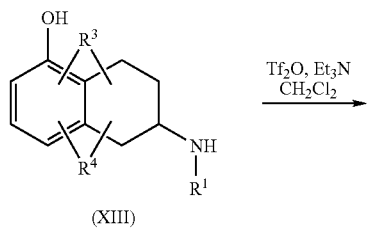

(XIII)

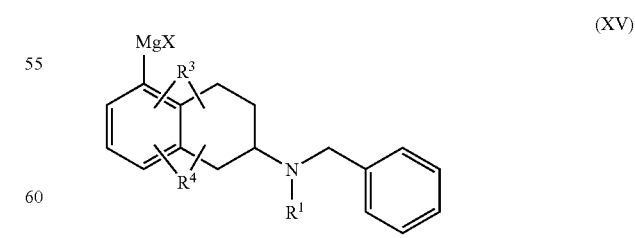

(XII)

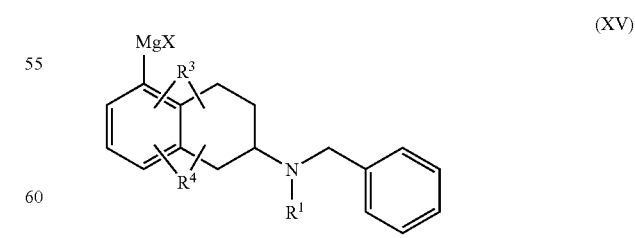

(I)

Preparation of enantiomerically pure compounds of general formula (S)-(I) can also be achieved by this alternative method when using compounds of general formula (S)-(VIa) as starting material. Compounds of general formula (S)-(VIa) can be obtained as described above (scheme 2B).

In a further aspect, the present invention also provides an alternative process for the preparation of intermediate compounds of general formula (II), which can be converted into the target compounds of general formula (I) following the methods described above (Scheme 1A). According to this process, at least one compound of general formula (XV), (XV)

wherein R¹, R³ and R⁴ have the meaning given above and X represents halogen, preferably bromide, is subjected to Kumada-Corriu cross-coupling reaction with at least one compound of general formula (XVI),

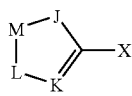

(XVI)

wherein K, L, M and J have the meaning given above and X represents halogen, preferably bromide, in a suitable reaction medium, in the presence of a palladium catalyst, a suitable ligand and at least one base.

Preparation of compounds of general formula (XV) can be achieved by Grignard reaction of compounds of general formula (IV),

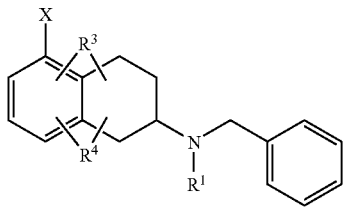

(IV)

wherein $R^1$, $R^3$ and $R^4$ have the meaning given above and X represents halogen, preferably bromide.

The compounds of general formula (XVI) are either commercially available or can be produced according to methods known to those skilled in the art.

The synthesis of compounds of general formula (IV) can be performed according to the methods described above (Scheme 1A).

Suitable reaction media are those described above.

The bases that may be used in the process are those described above.

This alternative method for the preparation of intermediate compounds of general formula (II) is illustrated in scheme 5:

Scheme 5

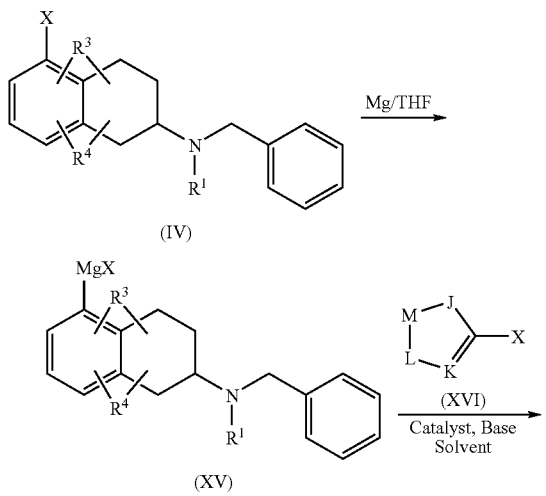

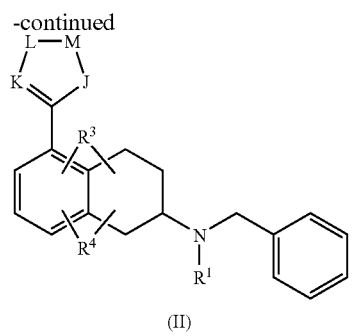

(II)

Preparation of enantiomerically pure compounds of general formula (S)-(I) can also be achieved by this alternative method when using compounds of general formula (S)-(IV) as starting material. Compounds of general formula (S)-(IV) can be obtained as described above (scheme 1B).

In another aspect, the present invention also provides an alternative process for the preparation of intermediate compounds of general formula (II), according to Scheme 6, wherein $R^1$, $R^3$, and $R^4$, have the meaning given above and K-L-M-J together form:

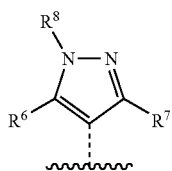

wherein $R^6$, $R^7$ and $R^8$ have the meaning described above. Compounds of general formula (II) can be converted into the target compounds of general formula (I) following the methods described above (Scheme 1A).

The compounds of general formula (XVII),

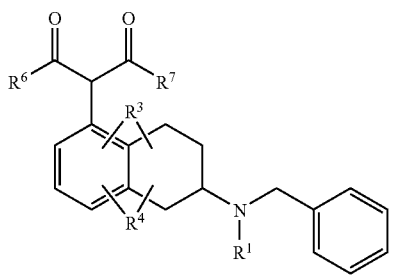

(XVII)

wherein $R^1$, $R^3$, $R^4$, $R^6$ and $R^7$ have the meaning described above are reacted with compounds of general formula (XVIII),

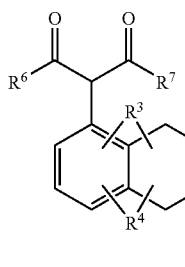

(XVIII)

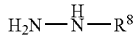

wherein $R^8$ has the meaning described above, in a suitable reaction media to give the title compounds of general formula (II).

Preparation of compounds of general formula (XVII) can be achieved by Cu catalyzed nucleophilic substitution reaction of compounds of general formula (XIX),

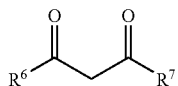

wherein $R^6$ and $R^7$ have the meaning described above, with compounds of general formula (IV),

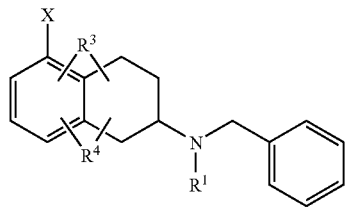

wherein $R^1$, $R^3$ and $R^4$ have the meaning given above and X represents halogen, preferably iodide or bromide in a suitable reaction medium, in the presence of CuX, and at least one base.

The compounds of general formulas (XVIII) and (XIX) are either commercially available or can be produced according to methods known to those skilled in the art.

Suitable reaction media are those described above.

The bases that may be used in the process are those descried above.

Starting compounds of general formula (IV) can be prepared according to Scheme 1A.

This alternative method for the preparation of compounds of general formula (I) is illustrated in scheme 6:

Scheme 6

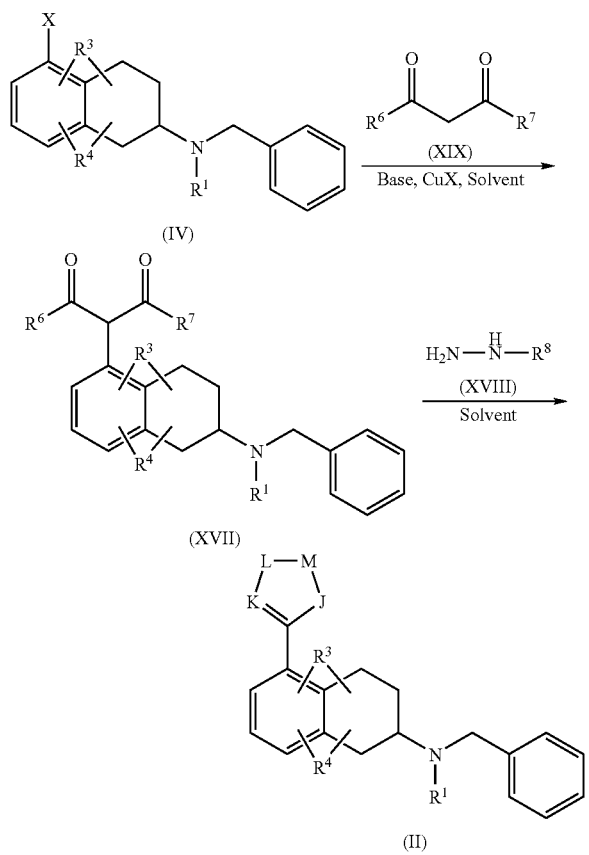

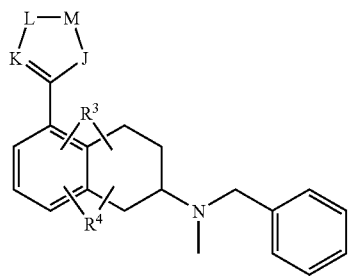

Preparation of enantiomerically pure compounds of general formula (S)-(I) can also be achieved by this alternative method when using compounds of general formula (S)-(IV) as starting material. Compounds of general formula (S)-(IV) can be obtained as described above (scheme 1B).

In a further aspect, the present invention also provides an alternative process for the preparation of compounds of general formula (I), according to scheme 7, in the particular case of $R^1$=–Me. According to this process, compounds of general formula (I) can be obtained by subjecting compounds of general formula (XX),

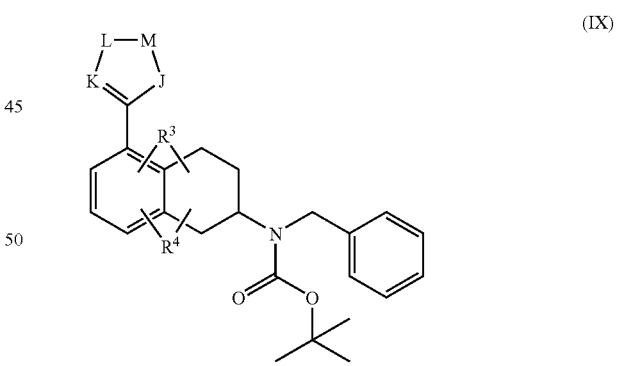

wherein K, L, M, J, $R^3$ and $R^4$ have the meaning given above, to benzyl cleavage by means of a hydrogenation reaction in the presence of a catalyst, especially a palladium catalyst, in a suitable reaction medium.

Compounds of general formula (XX) can be prepared by treatment of compounds of general formula (IX) with a reducing agent in a suitable reaction media, wherein K, L, M, J, $R^3$ and $R^4$ have the meaning given above.

Compounds of general formula (IX) are obtained from compounds of general formula (VIa) as described above (scheme 3).

Suitable reaction media are those described above.

The bases and reducing agents that may be used in the process are those described above.

The preparation of compounds of general formula (I) in the particular case in which $R^1$ is a methyl group, is illustrated in scheme 7:

Scheme 7

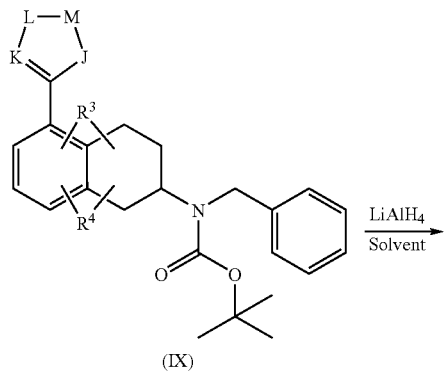

(IX)

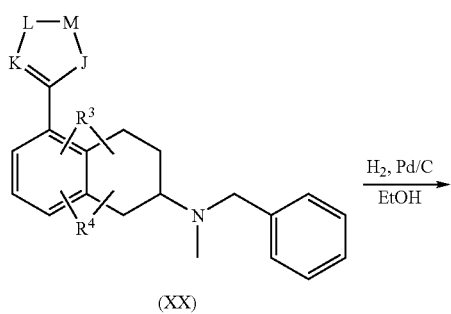

(XX)

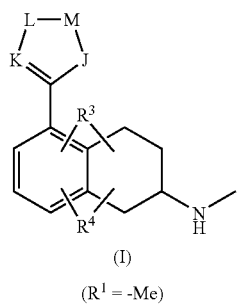

(I)
($R^1$ = -Me)

Preparation of enantiomerically pure compounds of general formula (S)-(I) can also be achieved by this alternative method when using compounds of general formula (S)-(IV) as starting material. Compounds of general formula (S)-(IV) can be obtained as described above (scheme 1B).

In a further aspect the present invention also provides processes for the enantioselective synthesis of compounds of general formula (S)-(I) and (R)-(I). Two of these methods are depicted in Schemes 8 and 9.

According to the process illustrated in Scheme 8, preparation of compounds of general formula (S)-(I) can be achieved by reaction of at least one compound of general formula (III) or (IIIa),

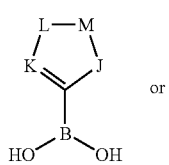

(III)

or

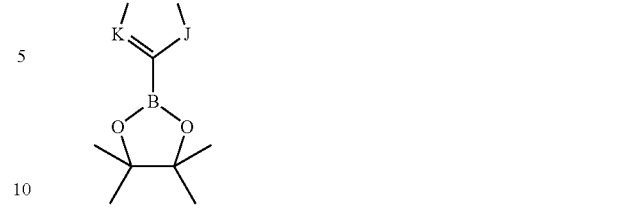

(IIIa)

wherein K, L, M and J have the meaning given above, by means of cross-coupling Suzuki reaction conditions with at least one compound of general formula (S)-(XII),

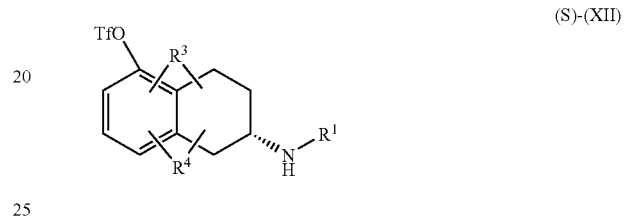

(S)-(XII)

wherein $R^1$, $R^3$, and $R^4$, have the meaning given above in a suitable reaction medium, in the presence of a palladium catalyst, a suitable ligand and at least one base.

Preparation of compounds of general formula (S)-(XII) can be achieved by reaction of triflic anhydride, in the presence of a base and in a suitable reaction medium, with compounds of general formula (S)-(XIII),

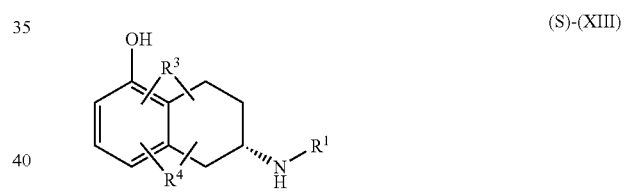

(S)-(XIII)

wherein $R^1$, $R^3$ and $R^4$ have the meaning described above.

Hydroxyl compounds of general formula (S)-(XIII) are obtained from the methoxy compounds of general formula (XXI) by heating in HBr 48% at 125° C.,

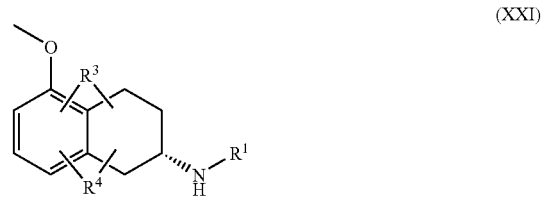

(XXI)

wherein $R^1$, $R^3$ and $R^4$ have the meaning described above.

Demethylation of compounds of general formula (XXI) to obtain compounds of general formula (S)-(XIII) can also be achieved by reaction with $BBr_3$ in a suitable reaction medium, or by other methods known to those skilled in the art.

Preparation of compounds of general formula (XXI) can be achieved by reductive amination reaction of aldehydes of general formula (V), $R^1$CHO           (V)

wherein R[1] have the meaning given above, with a compound of general formula (XXII),

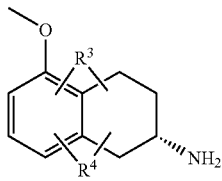
(XXII)

wherein R[3] and R[4] have the meaning described above. The reductive amination reaction could be performed following the methods described above.

Compounds of general formula (XXII) are obtained by palladium catalyzed hydrogenation of azide compounds of general formula (XXIII),

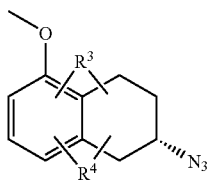
(XXIII)

wherein R[3] and R[4] have the meaning given above.

Compounds of general formula (XXIII) can be prepared by treatment with sodium azide in a suitable reaction medium of compounds of general formula (XXIV),

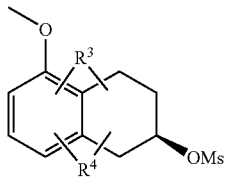
(XXIV)

wherein R[3] and R[4] have the meaning given above.

Hydroxyl compounds of general formula (XXV),

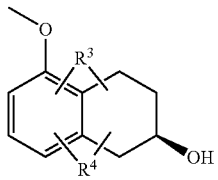
(XXV)

wherein R[3] and R[4] have the meaning described above are converted into the corresponding methanesulfonate compounds of general formula (XXIV) by treatment with methanesulfonyl chloride in a suitable reaction medium and in the presence of at least one base.

Compounds of general formula (XXV) are obtained by regioselective epoxide ring opening of compounds of general formula (XXVI),

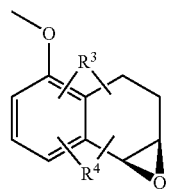
(XXVI)

wherein R[3] and R[4] have the meaning described above, in the presence of a reducing agent and in a suitable reaction medium.

Chiral epoxides of general formula (XXVI) are prepared from dihydronaphtalene compounds of general formula (XXVII),

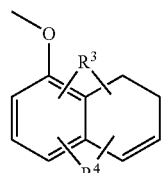
(XXVII)

wherein R[3] and R[4] have the meaning described above, in the conditions for the Jacobsen epoxidation known to those skilled in the art.

The compounds of general formulas (III), (IIIa), (V) and (XXVII) are either commercially available or can be produced according to methods known to those skilled in the art.

Suitable reaction media are those described above.

The bases and reducing agents that may be used in the process are those described above.

This enantioselective method for the preparation of compounds of general formula (S)-(I) is illustrated in scheme 8:

Scheme 8

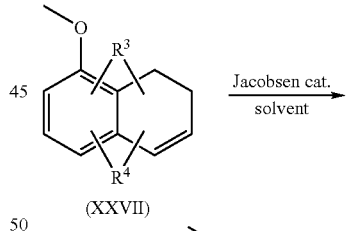

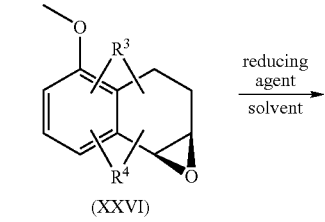

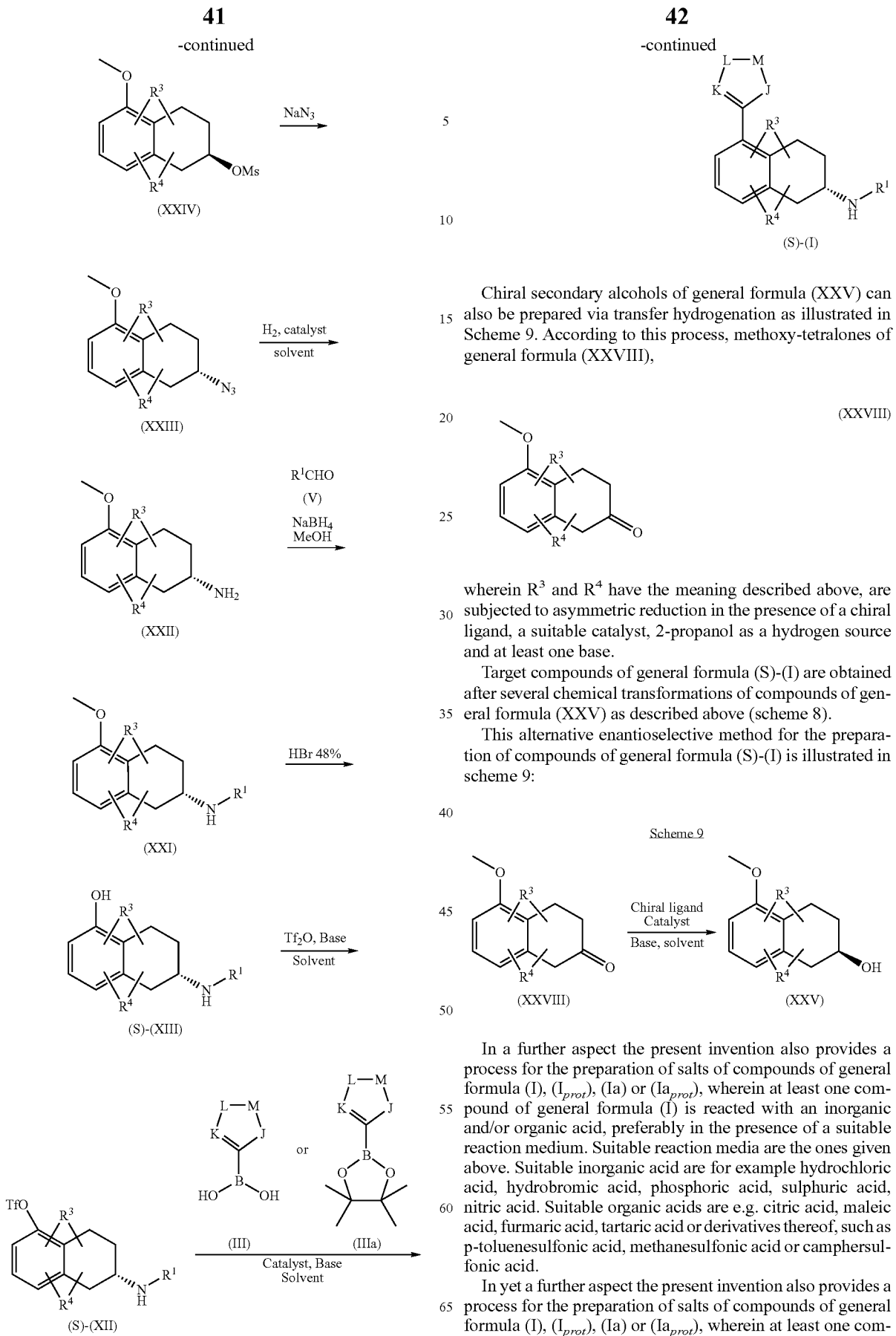

Chiral secondary alcohols of general formula (XXV) can also be prepared via transfer hydrogenation as illustrated in Scheme 9. According to this process, methoxy-tetralones of general formula (XXVIII), wherein $R^3$ and $R^4$ have the meaning described above, are subjected to asymmetric reduction in the presence of a chiral ligand, a suitable catalyst, 2-propanol as a hydrogen source and at least one base.

Target compounds of general formula (S)-(I) are obtained after several chemical transformations of compounds of general formula (XXV) as described above (scheme 8).

This alternative enantioselective method for the preparation of compounds of general formula (S)-(I) is illustrated in scheme 9:

In a further aspect the present invention also provides a process for the preparation of salts of compounds of general formula (I), $(I_{prot})$, (Ia) or $(Ia_{prot})$, wherein at least one compound of general formula (I) is reacted with an inorganic and/or organic acid, preferably in the presence of a suitable reaction medium. Suitable reaction media are the ones given above. Suitable inorganic acid are for example hydrochloric acid, hydrobromic acid, phosphoric acid, sulphuric acid, nitric acid. Suitable organic acids are e.g. citric acid, maleic acid, fumaric acid, tartaric acid or derivatives thereof, such as p-toluenesulfonic acid, methanesulfonic acid or camphersulfonic acid.

In yet a further aspect the present invention also provides a process for the preparation of salts of compounds of general formula (I), $(I_{prot})$, (Ia) or $(Ia_{prot})$, wherein at least one compound of general formula (I) having at least one acidic group is reacted with one or more suitable bases, preferably in the presence of suitable reaction medium. Suitable bases are e.g. hydroxides. Carbonates or alkoxides, which include suitable cations, derived e.g. from alkaline metals, alkaline earth metals or organic cations, e.g. $[NH_nR_{4-n}]^+$, wherein n is 0, 1, 2, 3 or 4 and R represents a branched or linear $C_{1-4}$ alkyl radical.

Solvates, preferably hydrates, of the phenylamino-substituted piperidine compounds of general formula (I), ($I_{prot}$), (Ia) or ($Ia_{prot}$), or corresponding stereoisomers, or corresponding salts may also be obtained by standard procedures known to those skilled in the art.

If the compounds of general formula (I), ($I_{prot}$), (Ia) or ($Ia_{prot}$), are obtained in form of a mixture of stereoisomers, particularly enantiomers or diastereomers, said mixtures may be separated by standard procedures known to those skilled in the art, e.g. chromatographic methods of crystallization with chiral reagents.

The purification and isolation of the phenylamino-substituted piperidine compounds of general formula (I), ($I_{prot}$) (Ia) or ($Ia_{prot}$), or a corresponding stereoisomer, or a corresponding salt, or corresponding solvate respectively, if required may be carried out by conventional methods known to those skilled in the art, e.g. chromatographic methods or recrystallization.

The compounds of general formula (I), ($I_{prot}$), (Ia) or ($Ia_{prot}$), their stereoisomers or the respective salts or solvates are toxicologically acceptable and are therefore suitable as pharmaceutical active substances for the preparation of medicaments.

The present invention therefore also provides for a medicament comprising at least one compound of general formula (I), ($I_{prot}$), (Ia) or ($Ia_{prot}$), optionally in form of one of its stereoisomers, preferably enantiomers or diastereomers, its racemate or in form of a mixture of at least two of its stereoisomers, preferably enantiomers or diastereomers, in any mixing ratio, or a physiologically acceptable salt thereof, or a solvate, respectively, and optionally one or more pharmaceutically acceptable adjuvants.

Furthermore, the present invention also provides for a pharmaceutical composition comprising at least one compound of general formula (I), ($I_{prot}$), (Ia) or ($Ia_{prot}$), optionally in form of one of its stereoisomers, preferably enantiomers or diastereomers, its racemate or in form of a mixture of at least two of its stereoisomers in any mixing ratio, or a physiologically acceptable salt thereof, or a solvate, respectively, and optionally one or more pharmaceutically acceptable adjuvants, which is not yet formulated into a medicament.

Preferably the medicament is suitable for the regulation of a 5-$HT_7$ mediated disease or condition.

The present invention also provides for the use of at least one compound of general formula (I), ($I_{prot}$), (Ia) or ($Ia_{prot}$) according to the invention, optionally in form of one of its stereoisomers, preferably enantiomers or diastereomers, its racemate or in form of a mixture of at least two of its stereoisomers, preferably enantiomers or diastereomers, in any mixing ratio, or a physiologically acceptable salt thereof, or a solvate, respectively, for the manufacture of a medicament for the treatment of a 5-$HT_7$ mediated disease or condition.

In a preferred embodiment the disease (or condition) is pain, preferably visceral pain, chronic pain, cancer pain, migraine, acute pain or neuropathic pain, more prefearably neuropathic pain, allodynia or hyperalgesia.

In a preferred embodiment the disease (or condition) is sleep disorder, shift worker syndrome, jet lag, depression, seasonal affective disorder, migraine, anxiety, psychosis, schizophrenia, cognition and memory disorders, neuronal degeneration resulting from ischemic events, cardiovascular diseases such as hypertension, irritable bowel syndrome, inflammatory bowel disease, spastic colon or urinary incontinence.

The medicament may be in any form suitable for the application to humans and/or animals, preferably mammals, and can be produced by standard procedures known to those skilled in the art. The composition of the medicament may vary depending on the route of administration.

The medicament of the present invention may e.g. be administered parentally in combination with conventional injectable liquid carriers, such as water or suitable alcohols. Conventional pharmaceutical adjuvants for injection, such as stabilizing agents, solubilizing agents, and buffers, may be included in such injectable compositions. These medicaments may preferably be injected intramuscularly, intraperitoneally, or intravenously.

Medicaments according to the present invention may also be formulated into orally administrable compositions containing one or more physiologically compatible carriers or excipients, in solid or liquid form. These compositions may contain conventional ingredients such as binding agents, fillers, lubricants, and acceptable wetting agents. The compositions may take any convenient form, such as tablets, pellets, capsules, lozenges, aqueous or oily solutions, suspensions, emulsions, or dry powdered form suitable for reconstitution with water or other suitable liquid medium before use, for immediate or controlled release.

The liquid oral forms for administration may also contain certain additives such as sweeteners, flavoring, preservatives, and emulsifying agents. Non-aqueous liquid compositions for oral administration may also be formulated, containing e.g. edible oils. Such liquid compositions may be conveniently encapsulated in e.g., gelatin capsules in a unit dosage amount.

The compositions of the present invention may also be administered topically or via a suppository.

The above mentioned compositions include preferably 1 to 60% by weight of one or more of the compound of general formula (I), optionally in form of one of its stereoisomers, preferably enantiomers or diastereomers, its racemate or in form of a mixture of at least two of its stereoisomers in any mixing ratio, or a physiologically acceptable salt thereof, or a solvate, respectively, and 40 to 99% by weight of the appropriate pharmaceutical vehicle(s).

The daily dosage for humans and animals may vary depending on factors that have their basis in the respective species or other factors, such as age, weight or degree of illness and so forth. The daily dosage for mammals including humans usally ranges from 1 milligram to 2000 milligram, preferably 1 to 1500 mg, more preferably 1 to 1000 mg of substance to be administered during one or several intakes.

Pharmacological Methods:

Radioligand Binding

Radioligand binding assays were performed using the Cloned Human Serotonin Receptor, Subtype 7 (h5$HT_7$), expressed in CHO cells, coated on Flashplate (Basic FlashPlate Cat.: SMP200) from PerkinElmer (Cat.: 6120512). The protocol assay was essentially the recommended protocol in the Technical Data Sheet by PerkinEmer Life and Analytical Sciences. The Mass membrane protein/well was typically 12 µg and the Receptor/well was about 9-10 fmoles. The Flashplate were let equilibrate at room temperature for one hour before the addition of the components of the assay mixture. The binding buffer was: 50 mM Tris-HCl, pH 7.4, containing 10 mM $MgCl_2$, 0.5 mM EDTA and 0.5% BSA. The radioligand was [$^{125}$I]LSD at a final concentration of 0.82 nM. Nonspecific binding was determined with 50 µM of Clozapine. The assay volume was 25 μl. TopSeal-A were applied onto Flashplate microplates and they were incubated at room temperature for 240 minutes in darkness. The radioactivity were quantified by liquid scintillation spectrophotometry (Wallac 1450 Microbeta Trilux) with a count delay of 4 minutes prior to counting and a counting time of 30 seconds per well. Competition binding data were analyzed by using the LIGAND program (Munson and Rodbard, LIGAND: A versatile, computerized approach for characterization of ligand-binding systems. *Anal. Biochem.* 107: 220-239, 1980) and assays were performed in triplicate determinations for each point.

The following examples are given to illustrate the present invention, but they do not limit the scope of the present invention.

EXAMPLES

Prepared according to above-described methods.

Chemical Example G (2S)-Methyl-[5-(1,3,5-trimethyl-1H-pyrazol-4-yl)-1,2,3,4-tetrahydro-naphthalen-2-yl]-amine

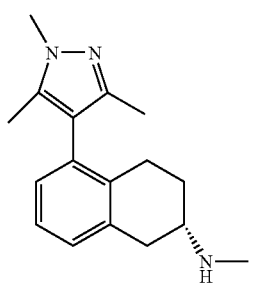

Methyl-[5-(1,3,5-trimethyl-1H-pyrazol-4-yl)-1,2,3,4-tetrahydro-naphthalen-2-yl]-amine Example G was prepared according to the following Scheme 2

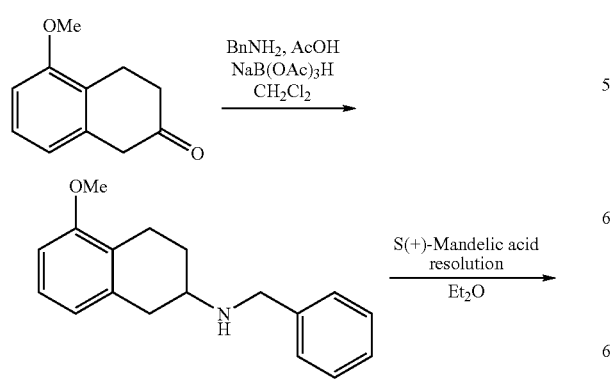

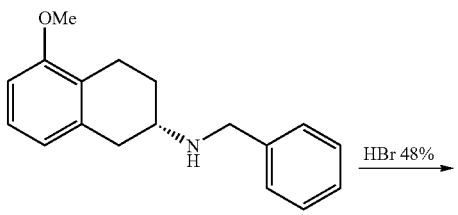

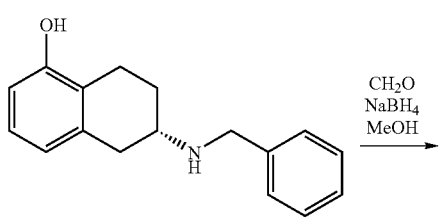

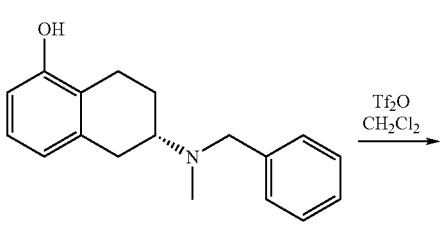

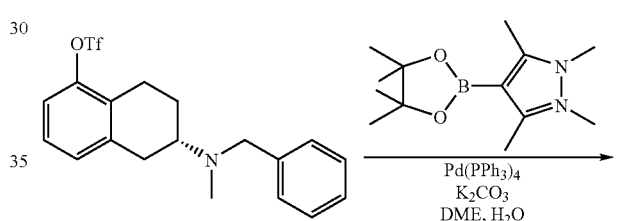

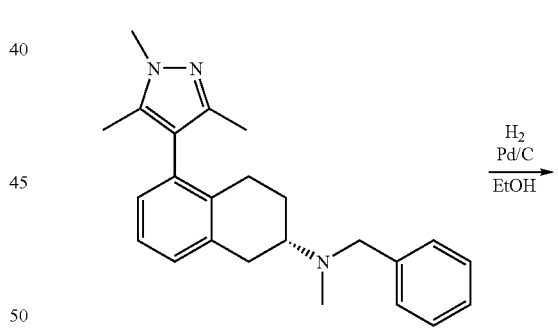

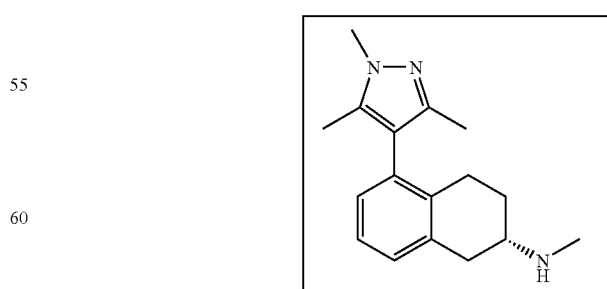

Step by step Example G was prepared as follows starting from Example A, whose precursor is readily available and may also be synthesized by anyone skilled in the art:

Example A

N-Benzyl-N-(5-methoxy-1,2,3,4-tetrahydronaphtha-len-2-yl)amine

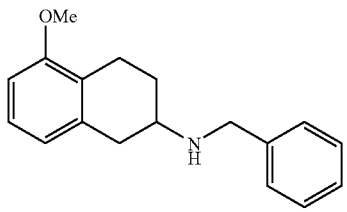

To a solution of 5-methoxy-2-tetralone (30 g, 170.24 mmol) dissolved in $CH_2Cl_2$ (250 mL) were added benzylamine (23 mL, 212.80 mmol) and AcOH (0.97 mL, 17.02 mmol), and the mixture was stirred for 4 h at room temperature. It was then cooled to 0° C. and $NaB(OAc)_3H$ (0.38 eq, 13.71 g, 64.69 mmol) was added over a period of 20 min. After 1 h stirring at 0° C., $NaB(OAc)_3H$ (1.07 eq, 38.61 g, 182.16 mmol) was added over a period of 30 min. It was added $CH_2Cl_2$ (100 mL), the reaction mixture warmed to room temperature and stirred for 15 h. The mixture was cooled again to 0° C., and $H_2O$ (200 mL) was added slowly. The pH of the solution was adjusted to 8.0 by adding $NaHCO_3$ saturated aqueous solution (300 mL), and the mixture was stirred at 0° C. for 15 min. The layers were separated, and the aqueous phase was extracted with $CH_2Cl_2$ (2×150 mL). All organic phases were combined, dried over anhydrous $Na_2SO_4$ and concentrated in vacuo. The residue (58.7 g) was purified by flash chromatography on silica gel (40:60:1-100:0:1 AcOEt/Hexane/$Et_3N$), followed by trituration with hexane, affording 33.87 g of the title compound (Rf=0.5 (10% MeOH/$CH_2Cl_2$), yellow solid, 74% yield).

$^1$H-NMR ($CDCl_3$, 250 MHz, δ): 7.26-7.12 (m, 5H, ArH); 7.00 (dd, J=8.0 y 7.7 Hz, 1H, ArH); 6.60 (m, 2H, ArH); 3.82 (s, 2H, $CH_2$); 3.72 (s, 3H, $CH_3$); 2.88 (m, 2H, $CH_2$); 2.51 (m, 2H, $CH_2$); 1.99 (m, 1H, CH); 1.48 (m, 2H, $CH_2$).

Example B

N-benzyl-N-[(2S)-5-methoxy-1,2,3,4-tetrahy-dronaphthalen-2-yl]amine

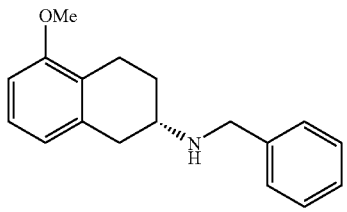

N-Benzyl-N-(5-methoxy-1,2,3,4-tetrahydronaphthalen-2-yl)amine (11.70 g, 43.76 mmol) was dissolved in $Et_2O$ (350 mL). The reaction mixture was warmed up to reflux and (S)-(+)-mandelic acid (6.66 g, 43.76 mmol) was added. It was added $CH_2Cl_2$ (30 mL), and the mixture was refluxed for 3 h. The mixture was cooled at room temperature, and stirred for 16 h. The resulting solid was filtered, washed with $Et_2O$ (3×20 mL) and dried to give 6.80 g of the diastereosiomeric salt as a white solid. The ee was evaluated in the compound (6S)-6-(dimethylamino)-5,6,7,8-tetrahydronaphthalen-1-ol (column chiralCel OD-H, 5 µm, 4.6×250 mm; flow rate: 1 ml/min; mobile phase: MeOH:EtOH (1:1)/hexanes 10:90).

The diastereosiomeric salt was recrystallized from $Et_2O$ to improve the ee. The salt was suspended in AcOEt (100 mL), and $K_2CO_3$ aqueous solution (20%, 80 mL) was added. The mixture was stirred at room temperature for 1 h and the layers were separated. The organic phase was dried over anhydrous $Na_2SO_4$ and concentrated in vacuo, affording 4.29 g of the title compound (Rf=0.5 (10% MeOH/$CH_2Cl_2$), pale yellow solid, 37% yield).

$^1$H-NMR ($CDCl_3$, 250 MHz, δ): 7.26-7.12 (m, 5H, ArH); 7.00 (dd, J=8.0 y 7.7 Hz, 1H, ArH); 6.60 (m, 2H, ArH); 3.82 (s, 2H, $CH_2$); 3.72 (s, 3H, $CH_3$); 2.88 (m, 2H, $CH_2$); 2.51 (m, 2H, $CH_2$); 1.99 (m, 1H, CH); 1.48 (m, 2H, $CH_2$).

Example C (6S)-6-[Benzyl(methyl)amino]-5,6,7,8-tetrahy-dronaphthalen-1-ol

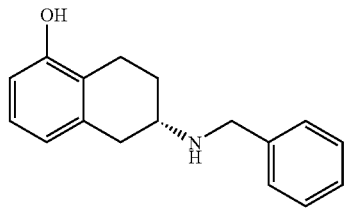

N-benzyl-N-[(2S)-5-methoxy-1,2,3,4-tetrahydronaphthalen-2-yl]amine (1.0 g, 3.74 mmol) was suspended in HBr aq. (48%, 70 mL), and the reaction mixture was refluxed for 4 h. The mixture was allowed to reach room temperature, and it was then cooled to −78° C. The pH of the solution was adjusted to 9.0 by adding $NH_3$ aqueous solution (25%) slowly. The mixture was allowed to reach room temperature, and was stirred for 30 min. The aqueous phase was extracted with $CHCl_3$ (3×100 mL). All organic phases were combined, dried over anhydrous $Na_2SO_4$ and concentrated in vacuo. The residue (1.0 g) was purified by flash chromatography on silica gel (10% MeOH/$CH_2Cl_2$), affording 0.86 g of the title compound (Rf=0.4 (10% MeOH/$CH_2Cl_2$), off-white solid, 91% yield).

$^1$H-NMR ($CDCl_3$, 250 MHz, δ): 9.13 (sa, 1H, OH); 7.38-7.17 (m, 5H, ArH); 6.86 (m, 1H, ArH); 6.54 (d, J=8.0 Hz, 1H, ArH); 6.47 (d, J=7.4 Hz, 1H, ArH); 3.80 (s, 2H, $CH_2$); 2.92-2.67 (m, 2H, $CH_2$); 2.41 (m, 2H, $CH_2$); 2.00 (m, 1H, CH); 1.45 (m, 2H, $CH_2$).

Example D (6S)-6[Benzyl(methyl)amino]-5,6,7,8-tetrahy-dronaphthalen-1-ol

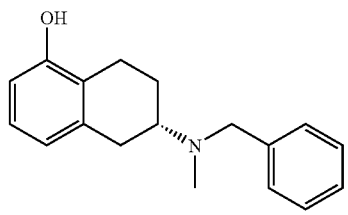

Formaldehyde (13.3 mL 37% aqueous solution, 13.3 mL, 177.62 mmol) and $NaBH_4$ (2.01 g, 53.29 mmol) were added in three portions (one portion every 20 min) to a 0° C. cooled solution of (6S)-6-[benzyl(methyl)amino]-5,6,7,8-tetrahydronaphthalen-1-ol (9.0 g, 35.52 mmol) in MeOH (400 mL). The reaction mixture was stirred at room temperature for 90 min, and solvent was concentrated off. The crude residue was diluted with $H_2O$ (150 mL) and extracted with AcOEt (2×150 mL). The organic layers were dried over anhydrous Na$_2$SO$_4$, filtered and concentrated. The crude was flash chromatographed on silica gel (100% AcOEt) to afford 7.13 g of the title compound (Rf=0.6 AcOEt/Hexano/Et$_3$N (10:10:2), white solid, 75% yield).

$^1$H-NMR (CDCl$_3$, 300 MHz, δ): 7.42-7.26 (m, 5H, ArH); 7.00 (m, 1H, ArH); 6.71 (d, J=7.6 Hz, 1H, ArH); 6.53 (d, J=7.6 Hz, 1H, ArH); 3.74 (m, 2H, CH$_2$); 3.07-2.88 (m, 4H, CH$_2$); 2.60 (m, 1H, CH); 2.34 (s, 3H, CH$_3$); 2.26 (m, 1H, CH); 1.73 (m, 1H, CH).

Example E (6S)-6-[Benzyl(methyl)amino]-5,6,7,8-tetrahydronaphthalen-1-yl trifluoromethanesulfonate

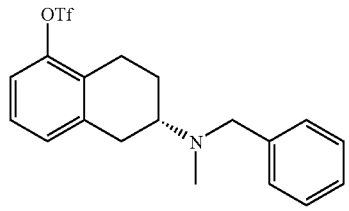

Tf$_2$O (3.6 mL, 21.309 mmol) was dropwise added to a −78° C. cooled solution of (6S)-6-[benzyl(methyl)amino]-5,6,7,8-tetrahydronaphthalen-1-ol (5.30 g, 19.822 mmol) and Et$_3$N (6 mL, 43.04 mmol) in CH$_2$Cl$_2$ (100 mL). Addition time: ca. 5 min. The reaction was completed after 15 min at low temperature (TLC analysis). The reaction mixture was poured into CH$_2$Cl$_2$ (250 mL) and washed with H$_2$O (200 mL). The organic layer was dried over anhydrous Na$_2$SO$_4$, filtered and concentrated. The crude residue was flash chromatographed on silica gel (1-2-3% MeOH/CH$_2$Cl$_2$), to furnish two batches of product: 5.78 g of pure triflate, and 1.90 g of product slightly impure (TLC analysis) (Rf=0.8 (10% MeOH/ CH$_2$Cl$_2$), off-white solid, 73% and 24% yield).

$^1$H-NMR (CDCl$_3$, 250 MHz, δ): 7.27-6.96 (m, 8H, ArH); 3.59 (m, 2H, CH$_2$); 3.07-2.56 (m, 5H, CH$_2$); 2.20 (s, 3H, CH$_3$); 2.14 (m, 1H, CH); 1.64 (m, 1H, CH).

Example F (2S)-Benzyl-methyl-[5-(1,3,5-trimethyl-1H-pyrazol-4-yl)-1,2,3,4-tetrahydro-naphthalen-2-yl]-amine

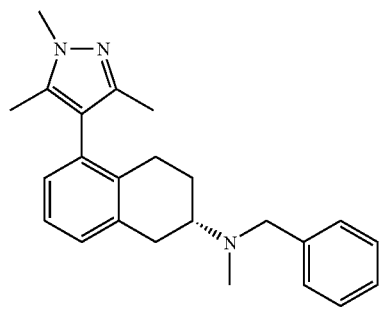

(6S)-6-[Benzyl(methyl)amino]-5,6,7,8-tetrahydronaphthalen-1-yl trifluoromethanesulfonate (5.0 g, 12.517 mmol), 1,3,5-trimethyl-1H-pyrazole-4-boronic acid pinacol ester (3.60 g, 15.246 mmol) and Pd(PPh$_3$)$_4$ (1.70 g, 1.471 mmol) were added to a solution of K$_2$CO$_3$ (3.31 g, 23.95 mmol) in a mixture of 1,2,-dimethoxyethane (120 mL) and H$_2$O (15 mL). The reaction mixture was purged with N$_2$ (g) for 10 min, and warmed up to reflux. The reaction was completed in 3 h (TLC analysis). It was allowed to reach room temperature, diluted with H$_2$O (150 mL) and extracted with AcOEt (300 mL). The organic layer was filtered through Celite (washing with AcOEt), dried over anhydrous Na$_2$SO$_4$, filtered and concentrated. The residue was purified by flash chromatography on silica gel (0-10-20% Et$_3$N/AcOEt) to afford the desired product as a brown-colored oil. The material was dissolved in CH$_2$Cl$_2$ (100 mL) and acidified with HCl aqueous solution (6 N). The organic layer was discarded, and the aqueous layer was taken to pH>13 with NaOH aqueous solution (6 N). It was extracted with CH$_2$Cl$_2$ (3×200 mL), and the organic layer was dried over anhydrous Na$_2$SO$_4$, filtered and concentrated, to give 3.67 g of the coupling product (Rf=0.3 (AcOEt), pale yellow oil, 81% yield).

$^1$H-NMR (CDCl$_3$, 250 MHz, δ): 7.29-7.00 (m, 7H, ArH); 6.82 (m, 1H, ArH); 3.70 (d, J=1.6 Hz, 3H, CH$_3$); 3.6 (d, J=3.3 Hz, 2H, CH$_2$); 2.90 (m, 4H, CH$_2$); 2.60-2.24 (m, 2H, CH$_2$); 2.20 (d, J=1.1 Hz, 3H, CH$_3$); 1.96 (d, J=1.4 Hz, 6H, CH$_3$); 1.93 (d, J=3.8 Hz, 6H, CH$_3$); 1.60 (m, 1H, CH). MS-EI+ m/z: 359.23

Example G (2S)-Methyl-[5-(1,3,5-trimethyl-1H-pyrazol-4-yl)-1,2,3,4-tetrahydro-naphthalen-2-yl]-amine

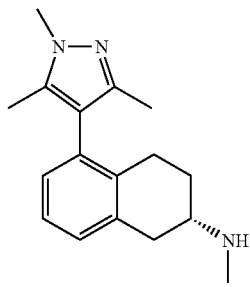

A solution of (2S)-benzyl-methyl-[5-(1,3,5-trimethyl-1 H-pyrazol-4-yl)-1,2,3,4-tetrahydro-naphthalen-2-yl]-amine (3.70 g, 10.291 mmol) in THF (20 mL) was added to Pd/C (1.20 g, 10% weight of Pd on activated carbon), and MeOH (120 mL) was added to the suspension. The reaction mixture was stirred under H$_2$ overnight (ca. 16 h). It was filtered through Celite washing with AcOEt (2×100 mL) and the solvent was concentrated off to give 2.54 g of the methylamine as pale brown oil. The crude was purified by flash chromatography on silica gel (10-20-60% MeOH/CH$_2$Cl$_2$), to yield 2.05 g of the title product (Rf=0.3 (AcOEt/MeOH/ Et$_3$N 20:3:2), pale yellow coloured oil, 74% yield).

$^1$H-NMR (CDCl$_3$, 250 MHz, δ): 7.11 (m, 2H, ArH); 6.92 (m, 1H, ArH); 3.77 (s, 3H, CH$_3$); 3.19 (m, 1H, CH); 3.08-2.81 (m, 2H, CH$_2$); 2.64-2.12 (m, 2H, CH$_2$); 2.60 (s, 3H, CH$_3$); 2.04 (m, 1H, CH); 2.02 (s, 3H, CH$_3$); 2.00 (d, J=2.2 Hz, 3H, CH$_3$); 1.55 (m, 1H, CH). MS-EI+ m/z: 269.19.

The other examples were then prepared as follows:

Example H (2S)-Methyl-[5-(1,3,5-trimethyl-1H-pyrazol-4-yl)-1,2,3,4-tetrahydro-naphthalen-2-yl]-amine dihydrochloride

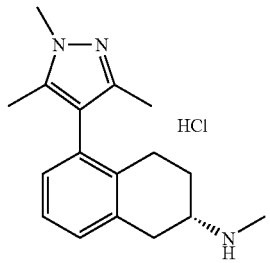

HCl (6.0 mL, 4 M solution in dioxane, 24.03 mmol) was dropwise added to a suspension of (2S)-methyl-[5-(1,3,5-trimethyl-1H-pyrazol-4-yl)-1,2,3,4-tetrahydro-naphthalen-2-yl]-amine (2.16 g, 8.01 mmol) in Et$_2$O (10 mL). The reaction mixture was stirred at room temperature for 2.5 h and then the solvent was concentrated off. The resulting solid was suspended in Et$_2$O (25 mL) and concentrated, in order to remove excess of HCl. This operation was done for three times, to give 2.42 g of the title product (Rf=0.3 (AcOEt/MeOH/Et$_3$N 20:3:2), white solid, 99% yield).

$^1$H-NMR (DMSO-d$_6$+D$_2$O, 250 MHz, δ): 9.31 (sa, 1H, NH); 7.19 (m, 2H, ArH); 6.95 (m, 1H, ArH); 3.80 (d, J=1.4 Hz, 3H, CH$_3$); 3.41-3.21 (m, 2H, CH$_2$); 2.96 (m, 1H, CH); 2.59 (m, 3H, CH$_3$); 2.44 (m, 2H, CH$_2$); 2.14 (m, 1H, CH); 2.05-1.97 (m, 6H, CH$_3$); 1.71 (m, 1H, CH).

Example I tert-Butyl benzyl [(2S)-5-hydroxy-1,2,3,4-tetrahydronaphthalen-2-yl]carbamate

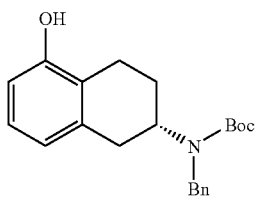

Boc$_2$O (0.380 g, 1.741 mmol) was added to a solution of (6S)-6-[benzyl(methyl)amino]-5,6,7,8-tetrahydronaphthalen-1-ol (Example C) (0.40 g, 1.578 mmol) and Et$_3$N (1.0 mL, 7.174 mmol) in CH$_2$Cl$_2$ (20 mL). The reaction mixture was stirred at room temperature for 8 h, poured into CH$_2$Cl$_2$ (200 mL) and washed with brine (1×100 mL). The organic layer was dried over anhydrous Na$_2$SO$_4$, filtered and concentrated. The crude residue was flash chromatographed on silica gel (5-10-20-30% AcOEt/Hexane) to give 0.44 g of the title product (Rf=0.8 (10% MeOH/CH$_2$Cl$_2$), white solid, 79% yield).

$^1$H-NMR (CDCl$_3$, 250 MHz, δ): 7.18 (m, 5H, ArH); 6.82 (m, 1H, ArH); 6.46 (d, J=7.7 Hz, 2H, ArH); 4.35 (sa, 2H, CH$_2$); 3.71 (m, 4H, CH$_2$); 2.44 (m, 1H, CH); 1.82-1.69 (m, 2H, CH$_2$); 1.33 (sa, 9H, CH$_3$)

Example J (6S)-6-[Benzyl(tert-butylcarbonyl)amino]-5,6,7,8-tetrahydronaphthalen-1-yl trifluoromethanesulfonate

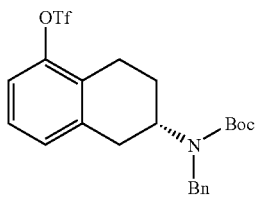

Tf$_2$O (0.270 mL, 1.598 mmol) was dropwise added to a −78° C. cooled solution of tert-butyl benzyl [(2S)-5-hydroxy-1,2,3,4-tetrahydronaphthalen-2-yl]carbamate (0.430 g, 1.217 mmol) and Et$_3$N (1.0 mL, 7.174 mmol) in CH$_2$Cl$_2$ (25 mL). The reaction was completed after 5 min at low temperature (TLC analysis). The reaction mixture was poured into H$_2$O (150 mL) and extracted with CH$_2$Cl$_2$ (1×150 mL). The organic layer was dried over anhydrous Na$_2$SO$_4$, filtered and concentrated. The crude residue was flash chromatographed on silica gel (10-20% AcOEt/Hexane) to furnish 0.508 g of the title product (Rf=0.8 (30% AcOEt/Hexane), colorless oil, 86% yield).

$^1$H-NMR (CDCl$_3$, 250 MHz, δ): 7.27 (m, 5H, ArH); 7.11 (m, 1H, ArH); 7.03 (m, 2H, ArH); 4.45 (sa, 2H, CH$_2$); 3.04-2.67 (m, 4H, CH$_2$); 1.97-1.70 (m, 3H, CH, CH$_2$); 1.44 (sa, 9H, CH$_3$)

Example K

N-Benzyl-N-tert-butylcarbonyl-N-[(2S)-5-(1,3,5-trimethyl-1H-pyrazol-4-yl)-1,2,3,4-tetrahydronaphthalen-2-yl]amine

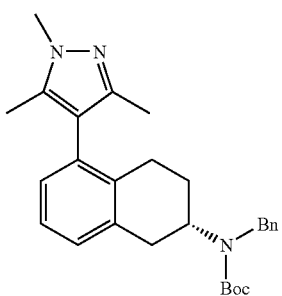

(6S)-6-[Benzyl(tert-butylcarbonyl)amino]-5,6,7,8-tetrahydronaphthalen-1-yl trifluoromethanesulfonate (0.5 g, 1.028 mmol), 1,3,5-trimethyl-1H-pyrazole-4-boronic acid pinacol ester (0.350 g, 1.482 mmol) and Pd(PPh$_3$)$_4$ (0.170 g, 0.147 mmol) were added to a solution of K$_2$CO$_3$ (0.30 g, 2.17 mmol) in a mixture of 1,2,-dimethoxyethane (30 mL) and H$_2$O (4 mL). The reaction mixture was purged with N$_2$ (g) for 10 min, and warmed up to reflux. The reaction was completed in 2 h. It was allowed to reach room temperature, diluted with AcOEt (300 mL) and filtered through Celite (washing with AcOEt). The organic layer was washed with brine (1×200 mL), dried over anhydrous Na$_2$SO$_4$, filtered and concentrated. The residue was purified by flash chromatography on silica gel (80-100% AcOEt/Hexane) to afford 0.38 g of the coupling product (Rf=0.1 (30% AcOEt/Hexane), viscous yellow oil, 83% yield).

$^1$H-NMR (CDCl$_3$, 250 MHz, δ): 7.27 (m, 5H, ArH); 7.09 (d, J=7.4 Hz, 1H, ArH); 7.01 (d, J=7.4 Hz, 1H, ArH); 7.88 (m, 1H, ArH); 4.44 (sa, 2H, CH$_2$); 3.75 (s, 3H, CH$_3$); 2.93 (m, 2H, CH$_2$); 2.45 (m, 2H, CH$_2$); 1.99 (m, 6H, CH$_3$); 1.77 (m, 1H, CH); 1.41 (sa, 9H, CH$_3$)

Example L (6S)-6-(Benzylamine)-5,6,7,8-tetrahydronaphthalen-1-yl trifluoromethanesulfonate

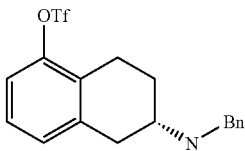

Tf$_2$O (0.620 mL, 3.734 mmol) was dropwise added to a −78° C. cooled solution of (6S)-6-[benzyl(methyl)amine]-5,6,7,8-tetrahydronaphthalen-1-ol (Example C) (0.860 g, 3.395 mmol) in CH$_2$Cl$_2$ (120 mL). The reaction was stirred at low temperature for 1.5 h. The reaction mixture was poured into H$_2$O (100 mL) and extracted with CH$_2$Cl$_2$ (2×50 mL). The organic layer was dried over anhydrous Na$_2$SO$_4$, filtered and concentrated. The crude residue was flash chromatographed on silica gel (1-5-10% MeOH/CH$_2$Cl$_2$), to furnish 0.279 g of triflate (Rf=0.8 (10% MeOH/CH$_2$Cl$_2$), orange colored oil, 21% yield).

$^1$H-NMR (CDCl$_3$, 250 MHz, δ): 7.28-7.11 (m, 5H, ArH); 7.14-6.97 (m, 3H, ArH); 3.83 (s, 2H, CH$_2$); 2.98 (m, 2H, CH$_2$); 2.63 (m, 1H, CH); 2.10 (m, 1H, CH); 1.57 (m, 3H, CH$_2$, CH)

Example M (2S)-Benzyl-[5-(1,3,5-trimethyl-1H-pyrazol-4-yl)-1,2,3,4-tetrahydro-naphthalen-2-yl]-amine

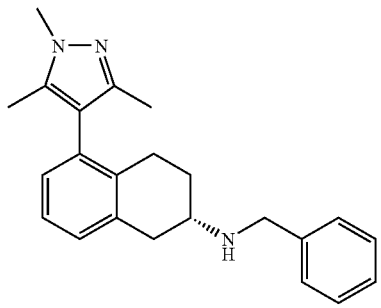

From (6S)-6-(benzylamine)-5,6,7,8-tetrahydronaphthalen-1-yl trifluoromethanesulfonate: Triflate, 1,3,5-trimethyl-1H-pyrazole-4-boronic acid pinacol ester (0.248 g, 1.051 mmol) and Pd(PPh$_3$)$_4$ (0.161 g, 0.140 mmol) were added to a solution of K$_2$CO$_3$ (0.194 g, 1.401 mmol) in a mixture of 1,2,-dimethoxyethane (30 mL) and H$_2$O (3 mL). The reaction mixture was purged with N$_2$ (g) for 10 min, and warmed up to reflux. The reaction was completed in 6 h. It was allowed to reach room temperature, diluted with H$_2$O (100 mL) and extracted with AcOEt (1×150 mL). The organic layer was filtered through Celite (washing with AcOEt), dried over anhydrous Na$_2$SO$_4$, filtered and concentrated. The residue was purified by flash chromatography on silica gel (0-5-10% MeOH/CH$_2$Cl$_2$) to afford 0.135 g of the coupling product (Rf=0.5 (10% MeOH/CH$_2$Cl$_2$), orange colored oil, 56% yield).

From N-benzyl-N-tert-butylcarbonyl-N-[(2S)-5-(1,3,5-trimethyl-1H-pyrazol-4-yl)-1,2,3,4-tetrahydronaphthalen-2-yl]amine: TFA (0.330 mL, 4.275 mmol) was added to a 0° C. cooled solution of starting material (0.381 g, 0.855 mmol) in CH$_2$Cl$_2$ (15 mL). The reaction was allowed to reach room temperature, and stirred at this temperature for 7 h. It was poured into H$_2$O (20 mL), extracted with CH$_2$Cl$_2$ (1×25 mL) and washed with NaOH aqueous solution (10%, 2×20 mL). The organic layer was dried over anhydrous Na$_2$SO$_4$, filtered and concentrated. The crude residue was flash chromatographed on silica gel (0-5-10% MeOH/CH$_2$Cl$_2$) to give 0.215 g of the title product (Rf=0.2 (10% MeOH/CH$_2$Cl$_2$), yellow oil, 73% yield).

$^1$H NMR (250 MHz, CHLOROFORM-d) δ ppm 1.50 (m, 2H) 1.94 (d, J=3.29 Hz, 3H) 1.97 (s, 3H) 2.19-2.53 (m, 2H) 2.66 (dd, J=15.09, 8.78 Hz, 1H) 2.82-3.14 (m, 2H) 3.70 (s, 3H) 3.84 (s, 2H) 6.84 (d, J=6.86 Hz, 1H) 6.95-7.11 (m, 2H) 7.20-7.31 (m, 5H). MS-FAB+ m/z: 346.32 (M+1).

Example N (2S)-5(1,3,5Trimethyl-1H-pyrazol-4-yl)-1,2,3,4tetrahydronaphthalen-2-amine

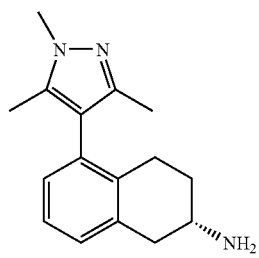

A solution of (2S)-benzyl-[5-(1,3,5-trimethyl-1H-pyrazol-4-yl)-1,2,3,4-tetrahydro-naphthalen-2-yl]-amine (0.287 g, 0.832 mmol) in THF (4 mL) was added to Pd/C (0.10 g, 10% weight of Pd on activated carbon), and MeOH (10 mL) was added to the suspension. The reaction mixture was stirred under H$_2$ (g) atmosphere (balloon) for 21 h. It was filtered through Celite washing with AcOEt (2×10 mL), the solvent was concentrated off and the crude was purified by flash chromatography on silica gel (CH$_2$Cl$_2$/MeOH/NH$_4$OH 95:5:1), to yield 0.178 g of the title product (Rf=0.2 (AcOEt/MeOH/Et$_3$N 20:3:2), pale yellow colored oil, 84% yield).

$^1$H-NMR (CDCl$_3$, 250 MHz, δ): 7.10 (m, 2H, ArH); 6.92 (m, 1H, ArH); 3.77 (d, J=1.4 Hz, 3H, CH$_3$); 3.11 (m, 2H, CH$_2$); 2.67-2.29 (m, 4H, CH$_2$); 1.93 (m, 6H, CH$_3$); 1.51 (m, 1H, CH).

Example O (2S)-5-(1,3,5Trimethyl-1H-pyrazol-4-yl)-1,2,3,4-tetrahydro-naphthalen-2-ylamine dihydrochloride

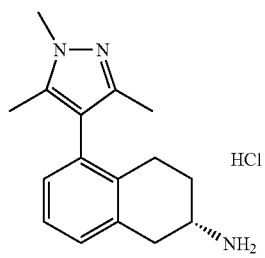

HCl (0.42 mL, 4 M solution in dioxane, 1.688 mmol) was dropwise added to a suspension of (2S)-5-(1,3,5-Trimethyl-1H-pyrazol-4-yl)-1,2,3,4-tetrahydronaphthalen-2-amine (0.143 g, 0.563 mmol) in Et$_2$O (5 mL). The reaction mixture was stirred at room temperature for 3 h and then the solvent was concentrated off. The resulting solid was suspended in Et$_2$O (10 mL) and concentrated, in order to remove excess of HCl. This operation was repeated for three times, to give 0.150 g of the title product (Rf=0.2 (AcOEt/MeOH/Et$_3$N 20:3:2), white solid, 91% yield).

$^1$H NMR (250 MHz, DMSO-d$_6$) δ ppm 1.56-1.76 (m, 1H) 1.94 (d, J=5.49 Hz, 3H) 2.01 (d, J=6.59 Hz, 3H) 2.07 (m, 1H) 2.45 (m, 2H) 2.85 (dd, J=16.05, 10.29 Hz, 1H) 3.15 (dd, J=16.05, 4.53 Hz, 1H) 3.41 (s, 1H) 3.74 (s, 3H) 6.92 (d, J=7.14 Hz, 1H) 7.03-7.26 (m, 2H) 8.21 (br, 2H). MS-FAB+ m/z: 256.06 (M+1-HCl).

Examples were or are prepared according to the reaction schemes and descriptions given above. The following table gives another overview of the examples:

| Example | Structure | Name | ¹H-NMR |
|---|---|---|---|
| Example H | 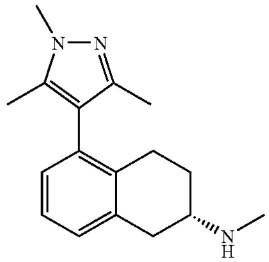 | (2S)-Methyl-[5-(1,3,5-trimethyl-1H-pyrazol-4-yl)-1,2,3,4-tetrahydro-naphthalen-2-yl]-amine | ¹H-NMR (DMSO-$d_6$ + $D_2O$, 250 MHz, δ): 9.31 (sa, 1 H, NH); 7.19 (m, 2 H, ArH); 6.95 (m, 1 H, ArH); 3.80 (d, J = 1.4 Hz, 3 H, $CH_3$); 3.41-3.21 (m, 2 H, $CH_2$); 2.96 (m, 1 H, CH); 2.59 (m, 3 H, $CH_3$); 2.44 (m, 2 H, $CH_2$); 2.14 (m, 1 H, CH); 2.05-1.97 (m, 6 H, $CH_3$); 1.71 (m, 1H, CH) (Dihydrochloride product) |
| Example M | 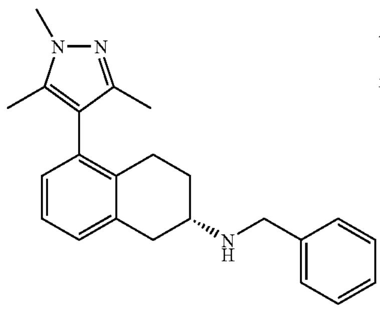 | (2S)-Benzyl-[5-(1,3,5-trimethyl-1H-pyrazol-4-yl)-1,2,3,4-tetrahydro-naphthalen-2-yl]-amine | ¹H NMR (250 MHz, CHLOROFORM-d) δ ppm 1.50 (m, 2 H) 1.94 (d, J = 3.29 Hz, 3 H) 1.97 (s, 3 H) 2.19-2.53 (m, 2 H) 2.66 (dd, J = 15.09, 8.78 Hz, 1 H) 2.82-3.14 (m, 2 H) 3.70 (s, 3 H) 3.84 (s, 2 H) 6.84 (d, J = 6.86 Hz, 1 H) 6.95-7.11 (m, 2 H) 7.20-7.31 (m, 5 H). |
| Example F | 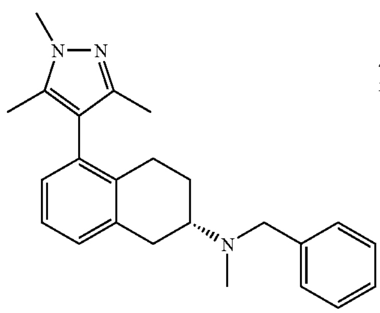 | (2S)-Benzyl-methyl-[5-(1,3,5-trimethyl-1H-pyrazol-4-yl)-1,2,3,4-tetrahydro-naphthalen-2-yl]-amine | ¹H NMR (250 MHz, CHLOROFORM-cl) δ ppm 7.29-7.00 (m, 7 H, ArH); 6.82 (m, 1 H, ArH); 3.70 (d, J =1.6 Hz, 3 H, $CH_3$); 3.6 (d, J = 3.3 Hz, 2 H, $CH_2$); 2.90 (m, 4 H, $CH_2$); 2.60 - 2.24 (m, 2 H, $CH_2$); 2.20 (d, J = 1.1 Hz, 3 H, $CH_3$); 1.96 (d, J = 1.4 Hz, 6 H, $CH_3$); 1.93 (d, J = 3.8 Hz, 6 H, $CH_3$); 1.60 (m, 1 H, CH). |
| Example O | 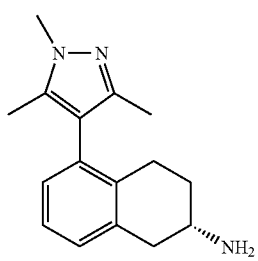 | (2S)-5-(1,3,5-Trimethyl-1H-pyrazol-4-yl)-1,2,3,4-tetrahydro-naphthalen-2-ylamine | ¹H NMR (250 MHz, DMSO-$d_6$) δ ppm 1.56-1.76 (m, 1 H) 1.94 (d, J = 5.49 Hz, 3 H) 2.01 (d, J = 6.59 Hz, 3 H) 2.07 (m, 1 H) 2.45 (m, 2 H) 2.85 (dd, J = 16.05, 10.29 Hz, 1 H) 3.15 (dd, J = 16.05, 4.53 Hz, 1 H) 3.41 (s, 1 H) 3.74 (s, 3 H) 6.92 (d, J = 7.14 Hz, 1 H) 7.03-7.26 (m, 2 H) 8.21 (br, 2 H). (Dichydrochloride product) |
| Example P | 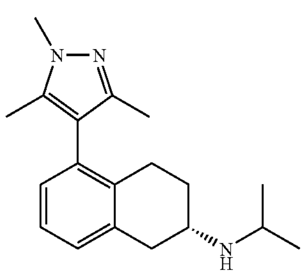 | (2S)-Isopropyl-[5-(1,3,5-trimethyl-1H-pyrazol-4-yl)-1,2,3,4-tetrahydro-naphthalen-2-yl]-amine | |

| Example | Structure | Name | ¹H-NMR |
|---------|-----------|------|--------|
| Example Q | 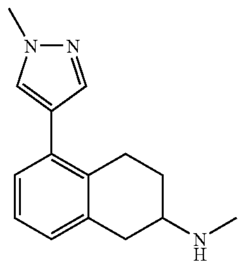 | Methyl-[5-(1-methyl-1H-pyrazol-4-yl)-1,2,3,4-tetrahydro-naphthalen-2-yl]-amine | |
| Example R | 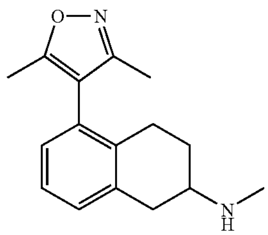 | [5-(3,5-Dimethyl-isoxazol-4-yl)-1,2,3,4-tetrahydro-naphthalen-2-yl]-methyl-amine | |
| Example S | 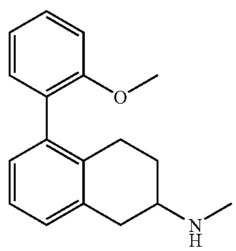 | [5-(2-Methoxy-phenyl)-1,2,3,4-tetrahydro-naphthalen-2-yl]-methyl-amine | |
| Example T | 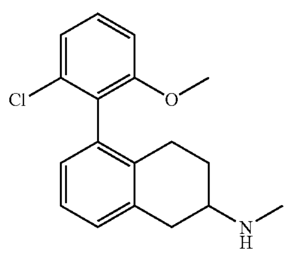 | [5-(2-Chloro-6-methoxy-phenyl)-1,2,3,4-tetrahydro-naphthalen-2-yl]-methyl-amine | |
| Example U | 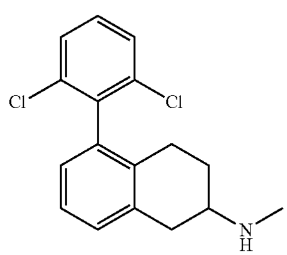 | [5-(2,6-Dichloro-phenyl)-1,2,3,4-tetrahydro-naphthalen-2-yl]-methyl-amine | |
| Example V | 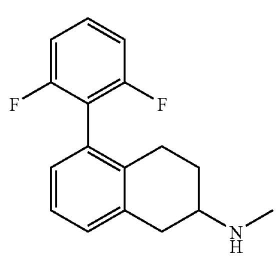 | [5-(2,6-Difluoro-phenyl)-1,2,3,4-tetrahydro-naphthalen-2-yl]-methyl-amine | |

-continued

| Example | Structure | Name | $^1$H-NMR |
|---|---|---|---|
| Example W | 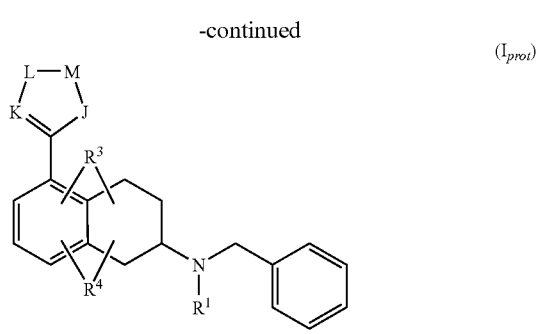 | [5-(2-Methoxy-pyridin-3-yl)-1,2,3,4-tetrahydro-naphthalen-2-yl]-methyl-amine | |

Pharmacological Data:

Results for representative compounds/examples are given in the table below:

| | COMPOUND | | | |
|---|---|---|---|---|
| EXAMPLE | 5-HT$_7$ IC$_{50}$ (nM) | 5-HT$_7$ %-Inhib. ($10^{-6}$ M) | 5-HT$_7$ %-Inhib. ($10^{-7}$ M) | 5-HT$_7$ %-Inhib. ($10^{-8}$ M) |
| H | 2.3 | 98.1 | 97.8 | 86.1 |
| F | 186.6 | 109.9 | 44.7 | 16.3 |
| O | 25.0 ± 3.8 | 79 | 47.2 | |
| P | 586.9 ± 10.0 | 61.7 | | |

Formulation Example

Example of a tablet formulation:

| | |
|---|---|
| Compound according to example H | 5 mg |
| Lactose | 60 mg |
| Crystalline cellulose | 25 mg |
| Povidone K 90 | 5 mg |
| Pregelanitized starch | 3 mg |
| Colloidal silica dioxide | 1 mg |
| Magnesium stearate | 1 mg |
| Total weight per tablet | 100 mg |

The above mentioned ingredients were mixed and compressed into a tablet by conventional methods known to those skilled in the art.

The invention claimed is:

1. A compound of general formula (I) or its benzyl-substituted analogue of general formula (I$_{prot}$), or a salt thereof,

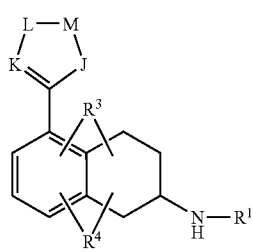

(I)

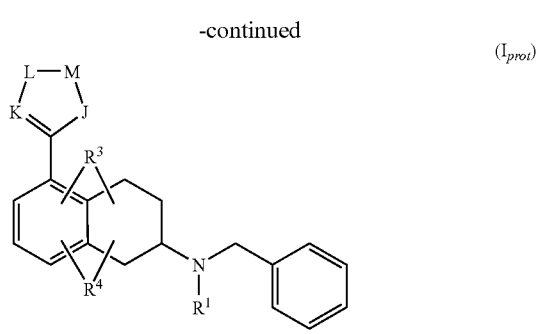

(I$_{prot}$)

wherein

K-L-M-J together form

=CH—X—Y=CH—, in which any suitable H may be substituted by R$^6$ or R$^7$, and in which X is selected from NR$^8$, O and S, while Y is selected from N and CH;

=CH—X—Y—C(O)—, in which any suitable H may be substituted by R$^6$ and in which one of X and Y is NR$^8$, while the other is selected from NR$^{8a}$, S and O;

=CH—X—Y—C(O)—, in which one of X and Y is CH$_2$, while the other is selected from NR$^8$, S or O, in which any suitable H may be substituted by R$^6$ or R$^7$;

=CR$^6$—N=N—C(O)—; or

=CR$^9$—X$_1$=Y—X$_2$=CR$^{9a}$, in which two of Y, X$_1$ and X$_2$ are CH, while the other is selected from CH and N, in which any suitable H may be substituted by R$^6$;

R$^1$ is selected from the group consisting of hydrogen; a linear or branched, saturated or unsaturated, optionally at least mono-substituted aliphatic radical; and an optionally at least mono-substituted alkyl-aryl;

R$^3$ and R$^4$ are independently from each other selected from hydrogen; halogen; OH; SH;

NH$_2$; a linear or branched, saturated or unsaturated, optionally at least mono-substituted aliphatic radical; and O—R with R being a linear or branched, saturated or unsaturated, optionally at least mono-substituted aliphatic radical;

R$^6$ and R$^7$ are independently from each other selected from hydrogen; halogen; OH; SH; NH$_2$; an aliphatic radical, which is linear or branched, saturated or unsaturated, and optionally at least mono-substituted by F, Cl, Br, I, SH or OH; and O—R with R being an aliphatic radical, which is linear or branched, saturated or unsaturated, and optionally at least mono-substituted by F, Cl, Br, I, SH or OH;

R$^8$ and R$^{8a}$ are independently from each other selected from hydrogen and an aliphatic radical, which is linear or branched, saturated or unsaturated, and optionally at least mono-substituted by F, Cl, Br, I, SH or OH;

R⁹ is selected from hydrogen; halogen; OH; SH; NH₂; an aliphatic radical, which is linear or branched, saturated or unsaturated, and optionally at least mono-substituted by F, Cl, Br, I, SH or OH; and O—R with R being an aliphatic radical, which is unsaturated linear or saturated or unsaturated branched, and optionally at least mono-substituted by F, Cl, Br, I, SH or OH;

R⁹ᵃ is selected from hydrogen; halogen; OH; SH; NH₂; an aliphatic radical, which is linear or branched, saturated or unsaturated, and optionally at least mono-substituted by F, Cl, Br, I, SH or OH; and O—R with R being an aliphatic radical, which is linear or branched, saturated or unsaturated, and optionally at least mono-substituted by F, Cl, Br, I, SH or OH;

with the following provisos if K-L-M-J together form =CR⁹—X₁=Y—X₂=CR⁹ᵃ, in which X₁ and X₂ are CH:

that if Y is CH, R³ and R⁴ are hydrogen, and R⁹ and R⁹ᵃ are OCH₃, then R¹ may not be hydrogen;

that if Y is CH, one of R³ or R⁴ is hydrogen, while the other is OCH₃, and one of R⁹ and R⁹ᵃ is hydrogen, while the other is Cl, then R¹ may not be methyl;

that if Y is CR⁶ with R⁶ being CF₃, one of R³ or R⁴ is hydrogen, while the other is OCH₃, and R⁹ and R⁹ᵃ are hydrogen, then R¹ may not be methyl; and that if Y is CH, one of R³ or R⁴ is hydrogen, while the other is OH, and R⁹ and R⁹ᵃ are hydrogen, then R¹ may not be hydrogen or iso-propyl.

2. A compound, or salt thereof, according to claim 1, characterized in that the compound is a compound according to formula Ia or of its benzyl-substituted analogue of general formula (Ia_{prot})

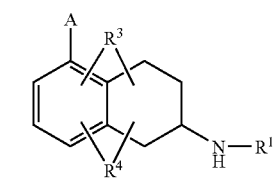
(Ia)

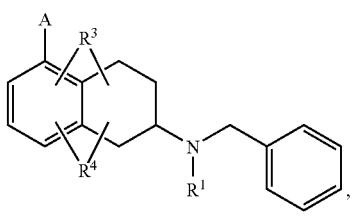
(Ia_{prot})

wherein
A is a compound selected from the following group

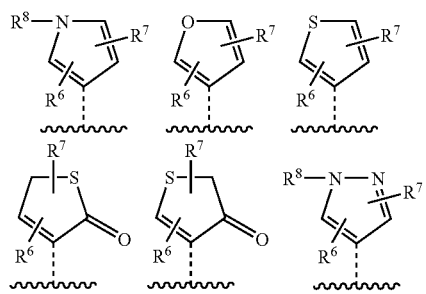

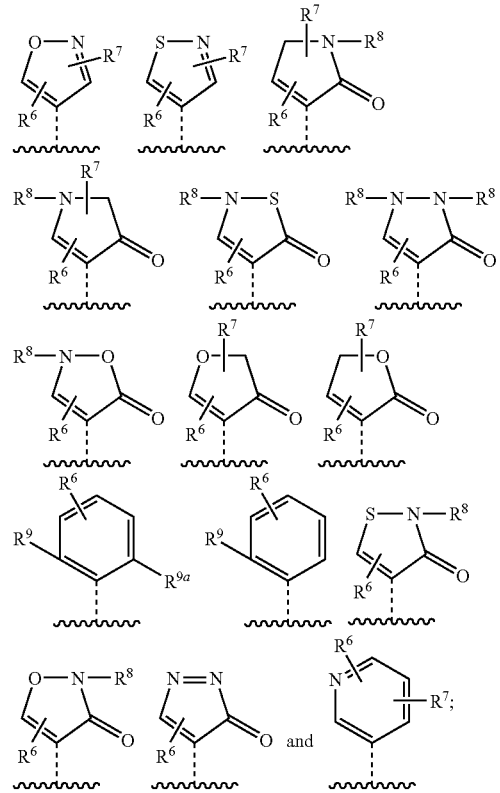

R¹ is selected from the group consisting of hydrogen; a linear or branched, saturated or unsaturated, optionally at least mono-substituted aliphatic radical; and an optionally at least mono-substituted alkyl-aryl;

R³ and R⁴ are independently from each other selected from hydrogen; halogen; OH; SH; NH₂; a linear or branched, saturated or unsaturated, optionally at least mono-substituted aliphatic radical; and O—R with R being a linear or branched, saturated or unsaturated, optionally at least mono-substituted aliphatic radical;

R⁶ and R⁷ are independently from each other selected from hydrogen; halogen; OH; SH; NH₂; an aliphatic radical, which is linear or branched, saturated or unsaturated, and optionally at least mono-substituted by F, Cl, Br, I, SH or OH; and O—R with R being an aliphatic radical, which is linear or branched, saturated or unsaturated, and optionally at least mono-substituted by F, Cl, Br, I, SH or OH;

R⁸ and R⁸ᵃ are independently from each other selected from hydrogen and an aliphatic radical, which is linear or branched, saturated or unsaturated, and optionally at least mono-substituted by F, Cl, Br, I, SH or OH;

R⁹ is selected from halogen; OH; SH; NH₂; an aliphatic radical, which is linear or branched, saturated or unsaturated, and optionally at least mono-substituted by F, Cl, Br, I, SH or OH; and O—R with R being an aliphatic radical, which is unsaturated linear or saturated or unsaturated branched, and optionally at least mono-substituted by F, Cl, Br, I, SH or OH;

R⁹ᵃ is selected from halogen; OH; SH; NH₂; an aliphatic radical, which is linear or branched, saturated or unsaturated, and optionally at least mono-substituted by F, Cl, Br, I, SH or OH; and O—R with R being an aliphatic radical, which is linear or branched, saturated or unsaturated, and optionally at least mono-substituted by F, Cl, Br, I, SH or OH;

with the following provisos applying if $R^6$ is hydrogen and A is

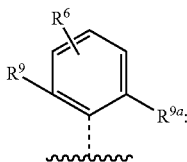

that if $R^3$ and $R^4$ are hydrogen, and $R^9$ and $R^{9a}$ are $OCH_3$, then $R^1$ may not be hydrogen; and that if one of $R^3$ or $R^4$ is hydrogen, while the other is $OCH_3$, and one of $R^9$ and $R^{9a}$ is hydrogen, while the other is Cl, then $R^1$ may not be methyl; and that if one of $R^3$ or $R^4$ is hydrogen, while the other is OH, and $R^9$ and $R^{9a}$ are hydrogen, then $R^1$ may not be hydrogen or iso-propyl.

3. A compound, or salt thereof, according to claim 2, characterized in that the compound is a compound according to Formula Ia, or $Ia_{prot}$ wherein A is a compound selected from the following group

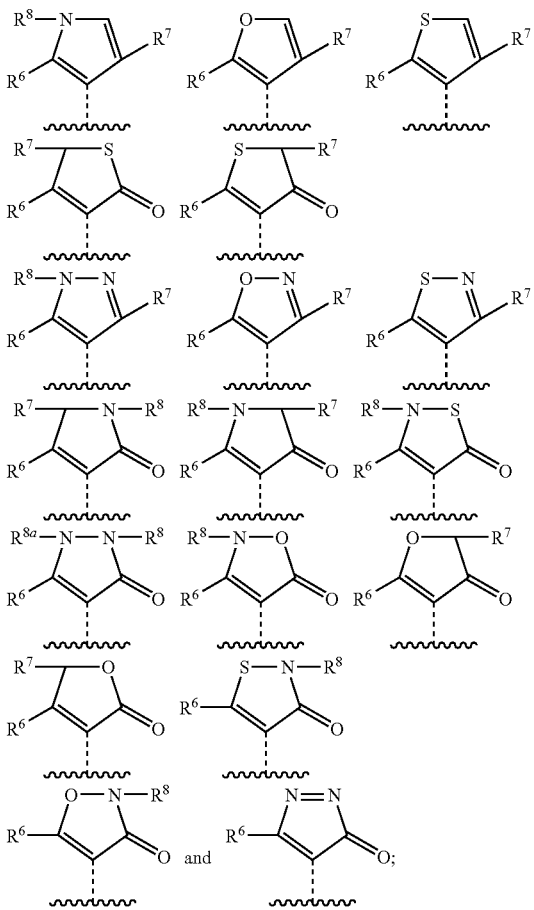

$R^1$ is selected from the group consisting of hydrogen and a linear or branched, saturated or unsaturated, optionally at least mono-substituted aliphatic radical;

$R^3$ and $R^4$ are independently from each other selected from hydrogen; halogen; OH; SH; $NH_2$; a linear or branched, saturated or unsaturated, optionally at least mono-substituted aliphatic radical; and O—R with R being a linear or branched, saturated or unsaturated, optionally at least mono-substituted aliphatic radical;

$R^6$ and $R^7$ are independently from each other selected from hydrogen; halogen; OH; SH; $NH_2$; an aliphatic radical, which is linear or branched, saturated or unsaturated, and optionally at least mono-substituted by F, Cl, Br, I, SH or OH; and O—R with R being an aliphatic radical, which is linear or branched, saturated or unsaturated, and optionally at least mono-substituted by F, Cl, Br, I, SH or OH; and $R^8$ and $R^{8a}$ are independently from each other selected from hydrogen and an aliphatic radical, which is linear or branched, saturated or unsaturated, and optionally at least mono-substituted by F, Cl, Br, I, SH or OH.

4. Compound, or salt thereof, according to claim 2, characterized in that the compound is a compound according to Formula Ia, or $Ia_{prot}$, wherein A is a compound selected from the following group

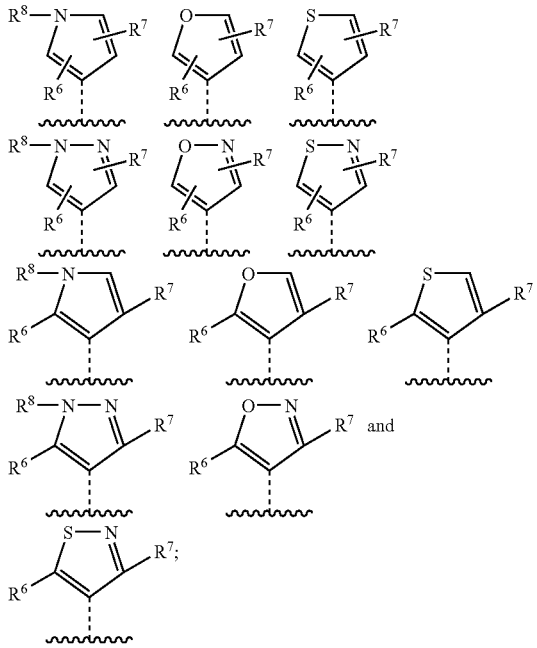

$R^1$ is selected from the group consisting of hydrogen; and a linear or branched, saturated or unsaturated, optionally at least mono-substituted aliphatic radical;

$R^3$ and $R^4$ are independently from each other selected from hydrogen; halogen; OH; SH; $NH_2$; a linear or branched, saturated or unsaturated, optionally at least mono-substituted aliphatic radical; and O—R with R being a linear or branched, saturated or unsaturated, optionally at least mono-substituted aliphatic radical;

$R^6$ and $R^7$ are independently from each other selected from hydrogen; halogen; OH; SH; $NH_2$; an aliphatic radical, which is linear or branched, saturated or unsaturated, and optionally at least mono-substituted by F, Cl, Br, I, SH or OH; and O—R with R being an aliphatic radical, which is linear or branched, saturated or unsaturated, and optionally at least mono-substituted by F, Cl, Br, I, SH or OH; and $R^8$ is selected from hydrogen and an aliphatic radical, which is linear or branched, saturated or unsaturated, and optionally at least mono-substituted by F, Cl, Br, I, SH or OH.

5. Compound, or salt thereof, according to claim 1, characterized in that $R^1$ is selected from the group consisting of hydrogen and a linear or branched, optionally at least mono-substituted $C_{1-4}$-alkyl radical.

6. Compound, or salt thereof, according to claim 5, characterized in that $R^1$ is selected from the group consisting of hydrogen and a linear or branched $C_{1-4}$-alkyl radical.

7. Compound, or salt thereof, according to claim 6, characterized in that $R^1$ is selected from the group consisting of hydrogen, $CH_3$, $C_2H_5$ and $C_3H_7$.

8. Compound, or salt thereof, according to claim 7, characterized in that $R^1$ is $CH_3$.

9. Compound, or salt thereof, according to claim 1, characterized in that $R^3$ and $R^4$ are independently from each other selected from hydrogen; halogen; OH; SH; $NH_2$; a linear or branched, optionally at least mono-substituted $C_{1-4}$-alkyl radical; and O—R with R being a linear or branched, optionally at least mono-substituted $C_{1-4}$-alkyl radical.

10. Compound, or salt thereof, according to claim 9, characterized in that $R^3$ and $R^4$ are independently from each other selected from H, F, Cl, Br, I, OH, SH, $NH_2$, $CH_3$, $C_2H_5$, $C_3H_7$, $C_4H_9$, $OCH_3$, $OC_2H_5$, $OC_3H_7$ and $OC_4H_9$.

11. Compound, or salt thereof, according to claim 10, characterized in that $R^3$ and $R^4$ are H.

12. Compound, or salt thereof, according to claim 1, characterized in that $R^6$ and $R^7$ are independently from each other selected from hydrogen; halogen; OH; SH; $NH_2$; a $C_{1-4}$-alkyl radical, which is linear or branched, and optionally at least mono-substituted by F, Cl, Br, I, SH or OH; and O—R with R being a $C_{1-4}$-alkyl radical, which is linear or branched, and optionally at least mono-substituted by F, Cl, Br, I, SH or OH.

13. Compound, or salt thereof, according to claim 12, characterized in that $R^6$ and $R^7$ are independently from each other selected from H, F, Cl, Br, I, OH, SH, $NH_2$, $CH_3$, $C_2H_5$, $C_3H_7$, $C_4H_9$, $OCH_3$, $OC_2H_5$, $OC_3H_7$ and $OC_4H_9$.

14. Compound, or salt thereof, according to claim 13, characterized in that $R^6$ and $R^7$ are independently from each other selected from H and $CH_3$.

15. Compound, or salt thereof, according to claim 1, characterized in that $R^8$ is selected from hydrogen and a $C_{1-4}$-alkyl radical, which is linear or branched, and optionally at least mono-substituted by F, Cl, Br, I, SH or OH.

16. Compound, or salt thereof, according to claim 15, characterized in that $R^8$ is selected from H, $CH_3$, $C_2H_5$, $C_3H_7$, and $C_4H_9$.

17. Compound, or salt thereof, according to claim 16, characterized in that $R^8$ is selected from H and $CH_3$.

18. Compound, or salt thereof, according to claim 2, characterized in that
A is selected from the following group

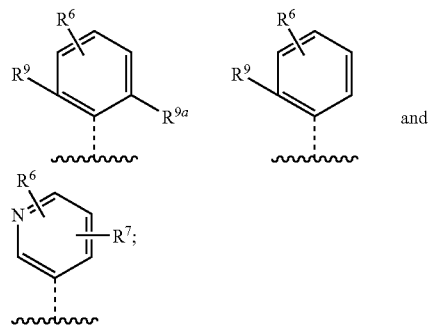

$R^1$ is selected from the group consisting of hydrogen and a linear or branched $C_{1-4}$-alkyl radical;

$R^3$ and $R^4$ are independently from each other selected from H, F, Cl, Br, I, OH, SH, $NH_2$, $CH_3$, $C_2H_5$, $C_3H_7$, $C_4H_9$, $OCH_3$, $OC_2H_5$, $OC_3H_7$ and $OC_4H_9$;

$R^6$ and $R^7$ are independently from each other selected from H, F, Cl, Br, I, OH, SH, $NH_2$, $CH_3$, $C_2H_5$, $C_3H_7$, $C_4H_9$, $OCH_3$, $OC_2H_5$, $OC_3H_7$ and $OC_4H_9$; and $R^9$ is selected from H, F, Cl, Br, I, OH, SH, $NH_2$, $CH_3$, $C_2H_5$, $C_3H_7$, and $C_4H_9$; and $R^{9a}$ is selected from H, F, Cl, Br, I, OH, SH, $NH_2$ $CH_3$, $C_2H_5$, $C_3H_7$, $C_4H_9$, $OCH_3$, $OC_2H_5$, $OC_3H_7$ and $OC_4H_9$.

19. Compound, or salt thereof, according to claim 18, characterized in that $R^1$ is $CH_3$.

20. Compound, or salt thereof, according to claim 18, characterized in that
$R^3$ and $R^4$ are H.

21. Compound, or salt thereof, according to claim 18, characterized in that $R^6$ and $R^7$ are independently from each other selected from H and $OCH_3$.

22. Compound, or salt thereof, according to claim 18, characterized in that $R^9$ is selected from H, Cl, and F, and $R^{9a}$ is selected from H, Cl, F, and $OCH_3$.

23. Compound, or salt thereof, according to claim 18, characterized in that
$R^1$ is $CH_3$;
$R^3$ and $R^4$ are H;
$R^6$ and $R^7$ are independently from each other selected from H and $OCH_3$;
$R^9$ is selected from H, Cl, and F; and
$R^{9a}$ is selected from H, Cl, F, and $OCH_3$.

24. Compound, or salt thereof, according to claim 1, selected from
Methyl-[5-(1,3,5-trimethyl-1H-pyrazol-4-yl)-1,2,3,4-tetrahydro-naphthalen-2-yl]-amine,
(2S)-Methyl-[5-(1,3,5-trimethyl-1H-pyrazol-4-yl)-1,2,3,4-tetrahydro-naphthalen-2-yl]-amine,
Benzyl[5-(1,3,5-trimethyl-1H-pyrazol-4-yl)-1,2,3,4-tetrahydro-naphthalen-2-yl]-amine,
(2S)-Benzyl-[5-(1,3,5-trimethyl-1H-pyrazol-4-yl)-1,2,3,4-tetrahydro-naphthalen-2-yl]-amine,
Benzyl-methyl-[5-(1,3,5-trimethyl-1H-pyrazol-4-yl)-1,2,3,4-tetrahydro-naphthalen-2-yl]-amine,
(2S)-Benzyl-methyl-[5-(1,3,5-trimethyl-1H-pyrazol-4-yl)-1,2,3,4-tetrahydro-naphthalen-2-yl]-amine;
5-(1,3,5-Trimethyl-1H-pyrazol-4-yl)-1,2,3,4-tetrahydro-naphthalen-2-ylamine;
(2S)-5-(1,3,5-Trimethyl-1H-pyrazol-4-yl)-1,2,3,4-tetrahydro-naphthalen-2-ylamine;
Isopropyl-[5-(1,3,5-trimethyl-1H-pyrazol-4-yl)-1,2,3,4-tetrahydro-naphthalen-2-yl]-amine;
(2S)-Isopropyl-[5-(1,3,5-trimethyl-1H-pyrazol-4-yl)-1,2,3,4-tetrahydro-naphthalen-2-yl]-amine;
Methyl-[5-(1-methyl-1H-pyrazol-4-yl)-1,2,3,4-tetrahydro-naphthalen-2-yl]-amine;
[5-(3,5-Dimethyl-isoxazol-4-yl)-1,2,3,4-tetrahydro-naphthalen-2-yl]-methyl-amine;
[5-(2-Methoxy-phenyl)-1,2,3,4-tetrahydro-naphthalen-2-yl]-methyl-amine;
[5-(2-Chloro-6-methoxy-phenyl)-1,2,3,4-tetrahydro-naphthalen-2-yl]-methyl-amine;
[5-(2,6-Dichloro-phenyl)-1,2,3,4-tetrahydro-naphthalen-2-yl]-methyl-amine;
[5-(2,6-Difluoro-phenyl)-1,2,3,4-tetrahydro-naphthalen-2-yl]-methyl-amine; and
[5-(2-Methoxy-pyridin-3-yl)-1,2,3,4-tetrahydro-naphthalen-2-yl]-methyl-amine.

25. Compound, or salt thereof, according to claim 24, selected from
(2S)-Methyl[5-(1,3,5-trimethyl-1H-pyrazol-4-yl)-1,2,3,4-tetrahydro-naphthalen-2-yl]amine and
(2S)-Benzyl-methyl[5-(1,3,5-trimethyl-1H-pyrazol-4-yl)-1,2,3,4-tetrahydro-naphthalen-2-yl]-amine.

26. Process for the preparation of compounds, or salts thereof, according to claim 1, characterized in that a compound of general formula II,

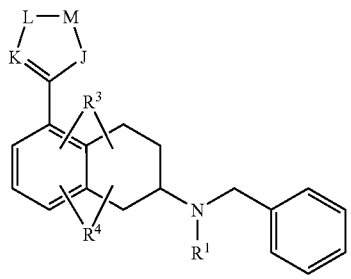
(II)

wherein $R^1$, $R^3$, $R^4$, K, L, M and J have the meaning according to claim 1, is subjected to benzyl cleavage by means of a hydrogenation reaction in the presence of a catalyst.

27. A process according to claim 26 wherein the catalyst is a palladium catalyst.

28. A composition comprising at least one compound, or salt thereof, according to claim 1 and optionally one or more pharmaceutically acceptable adjuvants.

29. A method for treating pain comprising administering to a subject in need thereof a therapeutically effective amount of at least one compound, or salt thereof, according to claim 1.

30. A method according to claim 29 wherein the pain is selected from visceral pain, chronic pain, cancer pain, migraine, acute pain, neuropathic pain, allodynia and hyperalgesia.

* * * * *